(12) United States Patent
Barzelay et al.

(10) Patent No.: US 9,305,334 B2
(45) Date of Patent: Apr. 5, 2016

(54) LUMINAL BACKGROUND CLEANING

(75) Inventors: Zohar Barzelay, Zichron Yaakov (IL);
Ran Cohen, Petach Tivka (IL); David Tolkowsky, Tel Aviv (IL)

(73) Assignee: SYNC-RX, LTD., Netanya (IL)

( * ) Notice: Subject to any disclaimer, the term of this patent is extended or adjusted under 35 U.S.C. 154(b) by 156 days.

(21) Appl. No.: 14/128,243

(22) PCT Filed: Jun. 21, 2012

(86) PCT No.: PCT/IL2012/000246
§ 371 (c)(1),
(2), (4) Date: Feb. 7, 2014

(87) PCT Pub. No.: WO2012/176191
PCT Pub. Date: Dec. 27, 2012

(65) Prior Publication Data
US 2014/0140597 A1    May 22, 2014

Related U.S. Application Data

(60) Provisional application No. 61/457,866, filed on Jun. 23, 2011.

(51) Int. Cl.
*G06K 9/00* (2006.01)
*G06T 5/00* (2006.01)
(Continued)

(52) U.S. Cl.
CPC . *G06T 5/001* (2013.01); *A61B 6/52* (2013.01); *A61B 6/5235* (2013.01); *G06T 5/009* (2013.01); *G06T 5/50* (2013.01); *A61B 6/481* (2013.01); *A61B 6/504* (2013.01); *A61B 6/5258* (2013.01);
(Continued)

(58) Field of Classification Search
None
See application file for complete search history.

(56) References Cited

U.S. PATENT DOCUMENTS 3,871,360 A    3/1975    Van Horn et al.
3,954,098 A    5/1976    Dick et al.
(Continued)

FOREIGN PATENT DOCUMENTS

EP    2 570 079 A1    3/2013
WO    94/10904    5/1994
(Continued)

OTHER PUBLICATIONS

Communication dated Sep. 5, 2014 from the USPTO in U.S. Appl. No. 14/143,289.
(Continued)

*Primary Examiner* — Li Liu
(74) *Attorney, Agent, or Firm* — Sughrue Mion, PLLC

(57) ABSTRACT

Apparatus and methods are described for use with an input angiogram image of a device inserted inside a portion of subject's body, the angiogram image being acquired in the presence of contrast agent. At least one processor (11) includes background-image-generation functionality (13) configured to generate a background image in which a relative value is assigned to a first pixel with respect to a second pixel, at least partially based upon relative values of surroundings of the first pixel and the surroundings of the second pixel in the input image. Cleaned-image-generation functionality (14) generates a cleaned image in which visibility of the radiopaque portions of the device is increased relative to the input image, by dividing the input image by the background image. Output-generation functionality (15) drives a display (16) to display an output based upon the cleaned image. Other applications are also described.

20 Claims, 5 Drawing Sheets

(51) Int. Cl.
*G06T 5/50* (2006.01)
*A61B 6/00* (2006.01)

(52) U.S. Cl.
CPC ............... *G06T 2207/10116* (2013.01); *G06T 2207/20212* (2013.01); *G06T 2207/30101* (2013.01)

(56) References Cited

U.S. PATENT DOCUMENTS

| | | | |
|---|---|---|---|
| 4,016,871 A | 4/1977 | Schiff |
| 4,031,884 A | 6/1977 | Henzel |
| 4,245,647 A | 1/1981 | Randall |
| 4,270,143 A | 5/1981 | Morris |
| 4,316,218 A | 2/1982 | Gay |
| 4,382,184 A | 5/1983 | Wernikoff |
| 4,545,390 A | 10/1985 | Leary |
| 4,709,385 A | 11/1987 | Pfeiler |
| 4,712,560 A | 12/1987 | Schaefer et al. |
| 4,723,938 A | 2/1988 | Goodin et al. |
| 4,741,328 A | 5/1988 | Gabbay |
| 4,758,223 A | 7/1988 | Rydell |
| 4,770,184 A | 9/1988 | Greene, Jr. et al. |
| 4,849,906 A | 7/1989 | Chodos et al. |
| 4,865,043 A | 9/1989 | Shimoni |
| 4,878,115 A | 10/1989 | Elion |
| 4,920,413 A | 4/1990 | Nakamura |
| 4,991,589 A | 2/1991 | Hongo et al. |
| 4,994,965 A | 2/1991 | Crawford et al. |
| 5,020,516 A | 6/1991 | Biondi |
| 5,054,045 A | 10/1991 | Whiting et al. |
| 5,054,492 A | 10/1991 | Scribner |
| 5,056,524 A | 10/1991 | Oe |
| 5,062,056 A | 10/1991 | Lo et al. |
| 5,150,292 A | 9/1992 | Hoffmann et al. |
| 5,176,619 A | 1/1993 | Segalowitz |
| 5,177,796 A | 1/1993 | Feig et al. |
| 5,293,574 A | 3/1994 | Roehm et al. |
| 5,295,486 A | 3/1994 | Wollschlager et al. |
| 5,330,496 A | 7/1994 | Alferness |
| 5,357,550 A | 10/1994 | Asahina et al. |
| 5,429,144 A | 7/1995 | Wilk |
| 5,457,728 A | 10/1995 | Whiting et al. |
| 5,457,754 A | 10/1995 | Han et al. |
| 5,486,192 A | 1/1996 | Walinsky et al. |
| 5,537,490 A | 7/1996 | Yukawa |
| 5,538,494 A | 7/1996 | Matsuda |
| 5,577,502 A | 11/1996 | Darrow et al. |
| 5,586,201 A | 12/1996 | Whiting et al. |
| 5,596,990 A | 1/1997 | Yock |
| 5,613,492 A | 3/1997 | Feinberg |
| 5,619,995 A | 4/1997 | Lobodzinski |
| 5,630,414 A | 5/1997 | Horbaschek |
| 5,674,217 A | 10/1997 | Wahlstrom et al. |
| 5,724,977 A | 3/1998 | Yock |
| 5,764,723 A | 6/1998 | Weinberger |
| 5,766,208 A | 6/1998 | McEwan |
| 5,792,157 A | 8/1998 | Mische et al. |
| 5,807,327 A | 9/1998 | Green et al. |
| 5,809,105 A | 9/1998 | Roehm et al. |
| 5,822,391 A | 10/1998 | Whiting et al. |
| 5,830,222 A | 11/1998 | Makower |
| 5,879,305 A | 3/1999 | Yock |
| 5,885,218 A | 3/1999 | Teo |
| 5,885,244 A | 3/1999 | Leone et al. |
| 5,916,194 A | 6/1999 | Jacobsen et al. |
| 5,921,934 A | 7/1999 | Teo |
| 5,971,976 A | 10/1999 | Wang et al. |
| 6,088,488 A | 7/2000 | Hardy et al. |
| 6,095,976 A | 8/2000 | Nachtomy |
| 6,120,455 A | 9/2000 | Teo |
| 6,120,523 A | 9/2000 | Crocker et al. |
| 6,126,608 A | 10/2000 | Kemme et al. |
| 6,148,095 A | 11/2000 | Prause et al. |
| 6,152,878 A | 11/2000 | Nachtomy |
| 6,195,445 B1 | 2/2001 | Dubuisson-Jolly et al. |
| 6,233,478 B1 | 5/2001 | Liu |
| 6,246,898 B1 | 6/2001 | Vesely et al. |
| 6,254,541 B1 | 7/2001 | Teo |
| 6,267,727 B1 | 7/2001 | Teo |
| 6,278,767 B1 | 8/2001 | Hsieh |
| 6,331,181 B1 | 12/2001 | Tierney et al. |
| 6,370,417 B1 | 4/2002 | Horbaschek et al. |
| 6,377,011 B1 | 4/2002 | Ben-Ur |
| 6,442,415 B1 | 8/2002 | Bis et al. |
| 6,454,715 B2 | 9/2002 | Teo |
| 6,454,776 B1 | 9/2002 | Tajima et al. |
| 6,473,635 B1 | 10/2002 | Rasche |
| 6,491,636 B2 | 12/2002 | Chenal |
| 6,493,575 B1 | 12/2002 | Kesten et al. |
| 6,496,716 B1 | 12/2002 | Langer et al. |
| 6,532,380 B1 | 3/2003 | Close et al. |
| 6,538,634 B1 | 3/2003 | Chui et al. |
| 6,546,271 B1 | 4/2003 | Reisfeld |
| 6,576,007 B2 | 6/2003 | Dehdashtian et al. |
| 6,589,176 B2 | 7/2003 | Jago |
| 6,616,596 B1 | 9/2003 | Milbocker |
| 6,643,533 B2 | 11/2003 | Knoplioch |
| 6,659,953 B1 | 12/2003 | Sumanaweera et al. |
| 6,666,863 B2 | 12/2003 | Wentzel et al. |
| 6,704,593 B2 | 3/2004 | Stainsby |
| 6,708,052 B1 | 3/2004 | Mao et al. |
| 6,711,436 B1 | 3/2004 | Duhaylongsod |
| 6,718,055 B1 | 4/2004 | Suri |
| 6,726,675 B1 | 4/2004 | Beyar |
| 6,728,566 B1 | 4/2004 | Subramanyan |
| 6,731,973 B2 | 5/2004 | Voith |
| 6,786,896 B1 | 9/2004 | Madhani et al. |
| 6,788,827 B1 | 9/2004 | Makram-Ebeid |
| 6,796,972 B1 | 9/2004 | Sinofsky et al. |
| 6,835,177 B2 | 12/2004 | Fritz et al. |
| 6,858,003 B2 | 2/2005 | Evans et al. |
| 6,912,471 B2 | 6/2005 | Heigl |
| 6,937,696 B1 | 8/2005 | Mostafavi |
| 6,959,266 B1 | 10/2005 | Mostafavi |
| 6,973,202 B2 | 12/2005 | Mostafavi |
| 6,980,675 B2 | 12/2005 | Evron et al. |
| 6,996,430 B1 | 2/2006 | Gilboa et al. |
| 6,999,852 B2 | 2/2006 | Green |
| 7,031,504 B1 | 4/2006 | Argiro et al. |
| 7,070,555 B2 | 7/2006 | Siess |
| 7,085,342 B2 | 8/2006 | Younis et al. |
| 7,134,994 B2 | 11/2006 | Alpert |
| 7,155,046 B2 | 12/2006 | Aben et al. |
| 7,155,315 B2 | 12/2006 | Niemeyer et al. |
| 7,180,976 B2 | 2/2007 | Wink et al. |
| 7,191,100 B2 | 3/2007 | Mostafavi |
| 7,209,779 B2 | 4/2007 | Kaufman |
| 7,215,802 B2 | 5/2007 | Klingensmith |
| 7,221,973 B2 | 5/2007 | Nitz |
| 7,269,457 B2 | 9/2007 | Shafer |
| 7,289,652 B2 | 10/2007 | Florent et al. |
| 7,321,677 B2 | 1/2008 | Evron et al. |
| 7,339,585 B2 | 3/2008 | Verstraelen et al. |
| 7,343,032 B2 | 3/2008 | Oakley et al. |
| 7,343,195 B2 | 3/2008 | Strommer et al. |
| 7,359,554 B2 | 4/2008 | Klingensmith |
| 7,369,691 B2 | 5/2008 | Kondo et al. |
| 7,397,935 B2 | 7/2008 | Kimmel |
| 7,398,116 B2 | 7/2008 | Edwards |
| 7,517,318 B2 | 4/2009 | Altmann |
| 7,546,154 B2 | 6/2009 | Hornegger et al. |
| 7,587,074 B2 | 9/2009 | Zarkh et al. |
| 7,599,730 B2 | 10/2009 | Hunter |
| 7,604,601 B2 | 10/2009 | Altmann |
| 7,650,179 B2 | 1/2010 | Redel et al. |
| 7,653,426 B2 | 1/2010 | Yatsuo et al. |
| 7,668,362 B2 | 2/2010 | Olson et al. |
| 7,693,349 B2 | 4/2010 | Gering |
| 7,697,974 B2 | 4/2010 | Jenkins |
| 7,713,210 B2 | 5/2010 | Byrd |
| 7,729,743 B2 | 6/2010 | Sabczynski et al. |
| 7,729,746 B2 | 6/2010 | Redel et al. |
| 7,740,584 B2 | 6/2010 | Donaldson |

(56) References Cited

U.S. PATENT DOCUMENTS

| | | |
|---|---|---|
| 7,742,629 B2 | 6/2010 | Zarkh et al. |
| 7,773,787 B2 | 8/2010 | Tek et al. |
| 7,773,792 B2 | 8/2010 | Kimmel |
| 7,778,488 B2 | 8/2010 | Nord |
| 7,778,688 B2 | 8/2010 | Strommer |
| 7,822,291 B2 | 10/2010 | Guetter |
| 7,831,076 B2 | 11/2010 | Altmann |
| 7,844,126 B2 | 11/2010 | Mory et al. |
| 7,848,553 B2 | 12/2010 | Hertel |
| 7,877,132 B2 | 1/2011 | Rongen |
| 7,889,905 B2 | 2/2011 | Higgins et al. |
| 7,892,177 B2 | 2/2011 | Rold et al. |
| 7,914,442 B1 | 3/2011 | Gazdzinski |
| 7,916,912 B2 | 3/2011 | Abramov et al. |
| 7,925,064 B2 | 4/2011 | Cloutier et al. |
| 7,925,069 B2 | 4/2011 | Ortyn et al. |
| 7,925,327 B2 | 4/2011 | Weese |
| 7,927,275 B2 | 4/2011 | Kuban |
| 7,930,014 B2 | 4/2011 | Huennekens et al. |
| 7,935,055 B2 | 5/2011 | Burckhardt |
| 7,961,926 B2 | 6/2011 | Viswanathan |
| 7,965,905 B2 | 6/2011 | Allon et al. |
| 7,970,187 B2 | 6/2011 | Puts |
| 7,978,916 B2 | 7/2011 | Klingensmith |
| 7,992,100 B2 | 8/2011 | Lundstrom |
| 8,025,622 B2 | 9/2011 | Rold et al. |
| 8,029,447 B2 | 10/2011 | Kanz |
| 8,052,605 B2 | 11/2011 | Muller |
| 8,055,327 B2 | 11/2011 | Strommer et al. |
| 8,077,939 B2 | 12/2011 | Le Bezet et al. |
| 8,080,474 B2 | 12/2011 | Chen |
| 8,086,000 B2 | 12/2011 | Weijers |
| 8,126,241 B2 | 2/2012 | Zarkh et al. |
| 8,155,411 B2 | 4/2012 | Hof |
| 8,157,742 B2 | 4/2012 | Taylor |
| 8,165,361 B2 | 4/2012 | Li |
| 8,172,763 B2 | 5/2012 | Nelson |
| 8,189,886 B2 | 5/2012 | Huo et al. |
| 8,199,981 B2 | 6/2012 | Koptenko et al. |
| 8,200,040 B2 | 6/2012 | Pfister |
| 8,208,995 B2 | 6/2012 | Tearney et al. |
| 8,213,676 B2 | 7/2012 | Bendall |
| 8,233,718 B2 | 7/2012 | Klingensmith |
| 8,260,395 B2 | 9/2012 | Markowitz et al. |
| 8,271,068 B2 | 9/2012 | Khamene |
| 8,275,201 B2 | 9/2012 | Rangwala et al. |
| 8,289,284 B2 | 10/2012 | Glynn |
| 8,295,577 B2 | 10/2012 | Zarkh et al. |
| 8,298,147 B2 | 10/2012 | Huennekens et al. |
| 8,303,503 B2 | 11/2012 | Nair |
| 8,364,242 B2 | 1/2013 | Li |
| 8,396,276 B2 | 3/2013 | Gatta |
| 8,396,533 B2 | 3/2013 | Barbu et al. |
| 8,409,098 B2 | 4/2013 | Olson |
| 8,411,927 B2 | 4/2013 | Chang et al. |
| 8,428,318 B2 | 4/2013 | Zhuo |
| 8,428,691 B2 | 4/2013 | Byrd |
| 8,433,115 B2 | 4/2013 | Chen |
| 8,457,374 B2 | 6/2013 | Lendl |
| 8,478,387 B2 | 7/2013 | Xu |
| 8,483,488 B2 | 7/2013 | Richter |
| 8,515,146 B2 | 8/2013 | Zhu et al. |
| 8,565,859 B2 | 10/2013 | Wang et al. |
| 8,605,976 B2 | 12/2013 | Diamant et al. |
| 8,625,865 B2 | 1/2014 | Zarkh et al. |
| 8,700,128 B2 | 4/2014 | Assis et al. |
| 8,731,642 B2 | 5/2014 | Zarkh et al. |
| 8,861,830 B2 | 10/2014 | Brada et al. |
| 2001/0031919 A1 | 10/2001 | Strommer et al. |
| 2001/0055418 A1 | 12/2001 | Nakamura |
| 2002/0049375 A1 | 4/2002 | Strommer et al. |
| 2002/0058869 A1 | 5/2002 | Axelsson et al. |
| 2002/0090119 A1 | 7/2002 | Saito et al. |
| 2002/0114497 A1 | 8/2002 | Wetzel et al. |
| 2002/0188307 A1 | 12/2002 | Pintor et al. |
| 2002/0193686 A1 | 12/2002 | Gilboa |
| 2003/0014100 A1 | 1/2003 | Maria Meens et al. |
| 2003/0018251 A1 | 1/2003 | Solomon |
| 2003/0021381 A1 | 1/2003 | Koppe et al. |
| 2003/0023141 A1 | 1/2003 | Stelzer et al. |
| 2003/0069499 A1 | 4/2003 | Lienard et al. |
| 2003/0088179 A1 | 5/2003 | Seeley et al. |
| 2003/0095710 A1 | 5/2003 | Tessadro |
| 2003/0139772 A1 | 7/2003 | Fisher et al. |
| 2003/0157073 A1 | 8/2003 | Peritt |
| 2004/0034380 A1 | 2/2004 | Woolfson et al. |
| 2004/0077941 A1 | 4/2004 | Reddy et al. |
| 2004/0097805 A1 | 5/2004 | Verard et al. |
| 2004/0133129 A1 | 7/2004 | Harari et al. |
| 2004/0165756 A1* | 8/2004 | Mielekamp .................. 382/130 |
| 2004/0176681 A1 | 9/2004 | Mao et al. |
| 2004/0215235 A1 | 10/2004 | Jackson et al. |
| 2004/0249270 A1 | 12/2004 | Kondo et al. |
| 2004/0254570 A1 | 12/2004 | Hadjicostis et al. |
| 2004/0267113 A1 | 12/2004 | Thomson |
| 2005/0004503 A1 | 1/2005 | Samson et al. |
| 2005/0008210 A1 | 1/2005 | Evron et al. |
| 2005/0015009 A1 | 1/2005 | Mourad et al. |
| 2005/0031176 A1 | 2/2005 | Hertel |
| 2005/0033199 A1 | 2/2005 | van der Steen |
| 2005/0043614 A1 | 2/2005 | Huizenga et al. |
| 2005/0054916 A1 | 3/2005 | Mostafavi |
| 2005/0067568 A1 | 3/2005 | Harding et al. |
| 2005/0080336 A1 | 4/2005 | Byrd et al. |
| 2005/0090737 A1 | 4/2005 | Burrel et al. |
| 2005/0096589 A1 | 5/2005 | Shachar |
| 2005/0107688 A1 | 5/2005 | Strommer |
| 2005/0107808 A1 | 5/2005 | Evans et al. |
| 2005/0111719 A1 | 5/2005 | Pesatore et al. |
| 2005/0113685 A1 | 5/2005 | Maschke et al. |
| 2005/0137661 A1 | 6/2005 | Sra |
| 2005/0141766 A1 | 6/2005 | Nagahashi et al. |
| 2005/0143777 A1 | 6/2005 | Sra |
| 2005/0154281 A1 | 7/2005 | Xue et al. |
| 2005/0182295 A1 | 8/2005 | Soper et al. |
| 2005/0197557 A1 | 9/2005 | Strommer et al. |
| 2005/0197559 A1 | 9/2005 | Boese et al. |
| 2005/0197566 A1 | 9/2005 | Strommer et al. |
| 2005/0201510 A1 | 9/2005 | Mostafavi |
| 2005/0228359 A1 | 10/2005 | Doyle |
| 2005/0234331 A1 | 10/2005 | Sendai |
| 2005/0273050 A1 | 12/2005 | Yokoyama et al. |
| 2005/0288577 A1 | 12/2005 | Weese |
| 2006/0007188 A1 | 1/2006 | Reiner |
| 2006/0058647 A1 | 3/2006 | Strommer et al. |
| 2006/0074285 A1 | 4/2006 | Zarkh et al. |
| 2006/0106318 A1 | 5/2006 | Davidson |
| 2006/0120581 A1 | 6/2006 | Eck et al. |
| 2006/0129142 A1 | 6/2006 | Reynolds |
| 2006/0147897 A1 | 7/2006 | Grinvald |
| 2006/0149134 A1 | 7/2006 | Soper et al. |
| 2006/0155327 A1 | 7/2006 | Briganti et al. |
| 2006/0159318 A1 | 7/2006 | Alyassin et al. |
| 2006/0165270 A1 | 7/2006 | Borgert et al. |
| 2006/0173287 A1 | 8/2006 | Sabczynski et al. |
| 2006/0184016 A1 | 8/2006 | Glossop |
| 2006/0188135 A1 | 8/2006 | Zarkh et al. |
| 2006/0193505 A1 | 8/2006 | Glukhovsky et al. |
| 2006/0224188 A1 | 10/2006 | Libbus et al. |
| 2006/0224232 A1 | 10/2006 | Chobotov |
| 2006/0241369 A1 | 10/2006 | Lienard et al. |
| 2006/0241445 A1 | 10/2006 | Altmann |
| 2006/0241465 A1 | 10/2006 | Huennekens et al. |
| 2006/0241478 A1 | 10/2006 | Lewis |
| 2006/0253024 A1 | 11/2006 | Altmann |
| 2006/0253029 A1 | 11/2006 | Altmann |
| 2006/0253031 A1 | 11/2006 | Altmann |
| 2006/0257006 A1 | 11/2006 | Bredno et al. |
| 2006/0259137 A1 | 11/2006 | Artof et al. |
| 2006/0269108 A1 | 11/2006 | Viswanathan |
| 2006/0287595 A1 | 12/2006 | Maschke |
| 2007/0021816 A1 | 1/2007 | Rudin |
| 2007/0038061 A1 | 2/2007 | Huennekens et al. |
| 2007/0038081 A1 | 2/2007 | Eck et al. |

(56) References Cited

U.S. PATENT DOCUMENTS

| | | |
|---|---|---|
| 2007/0043292 A1 | 2/2007 | Camus |
| 2007/0053558 A1 | 3/2007 | Puts et al. |
| 2007/0055128 A1 | 3/2007 | Glossop |
| 2007/0060798 A1 | 3/2007 | Krupnik et al. |
| 2007/0088431 A1 | 4/2007 | Bourang et al. |
| 2007/0106146 A1 | 5/2007 | Altmann et al. |
| 2007/0116342 A1 | 5/2007 | Zarkh et al. |
| 2007/0123771 A1 | 5/2007 | Redel et al. |
| 2007/0142907 A1 | 6/2007 | Moaddeb et al. |
| 2007/0147706 A1 | 6/2007 | Sasaki et al. |
| 2007/0165916 A1 | 7/2007 | Cloutier et al. |
| 2007/0173861 A1 | 7/2007 | Strommer |
| 2007/0208388 A1 | 9/2007 | Jahns |
| 2007/0219630 A1 | 9/2007 | Chu |
| 2007/0232896 A1 | 10/2007 | Gilboa et al. |
| 2007/0248253 A1 | 10/2007 | Manzke et al. |
| 2007/0255139 A1 | 11/2007 | Deschinger |
| 2007/0269135 A1 | 11/2007 | Ono |
| 2007/0276216 A1 | 11/2007 | Beyar et al. |
| 2008/0008366 A1 | 1/2008 | Desh |
| 2008/0015677 A1 | 1/2008 | Glossop et al. |
| 2008/0021331 A1 | 1/2008 | Grinvald |
| 2008/0082049 A1 | 4/2008 | Evans et al. |
| 2008/0089566 A1 | 4/2008 | Node-Langlois |
| 2008/0114238 A1 | 5/2008 | Lloyd |
| 2008/0118117 A1 | 5/2008 | Gauldie et al. |
| 2008/0119922 A1 | 5/2008 | Alkhatib |
| 2008/0137923 A1 | 6/2008 | Spahn |
| 2008/0137935 A1 | 6/2008 | Spahn |
| 2008/0146923 A1 | 6/2008 | Mejia |
| 2008/0146942 A1 | 6/2008 | Dala-Krishna |
| 2008/0177183 A1 | 7/2008 | Courtney |
| 2008/0188739 A1 | 8/2008 | Rongen et al. |
| 2008/0221439 A1 | 9/2008 | Iddan et al. |
| 2008/0221440 A1 | 9/2008 | Iddan et al. |
| 2008/0221442 A1 | 9/2008 | Tolkowsky et al. |
| 2008/0247621 A1 | 10/2008 | Zarkh et al. |
| 2008/0253686 A1 | 10/2008 | Bayer |
| 2008/0262346 A1 | 10/2008 | Assis et al. |
| 2008/0267475 A1 | 10/2008 | Lendl |
| 2008/0283771 A1 | 11/2008 | Li |
| 2008/0300487 A1 | 12/2008 | Govari |
| 2009/0016587 A1 | 1/2009 | Strobel et al. |
| 2009/0074284 A1 | 3/2009 | Zeineh et al. |
| 2009/0093676 A1 | 4/2009 | Davidson |
| 2009/0103682 A1 | 4/2009 | Chen et al. |
| 2009/0105579 A1 | 4/2009 | Garibaldi |
| 2009/0116715 A1 | 5/2009 | Bredno et al. |
| 2009/0171201 A1 | 7/2009 | Olson |
| 2009/0177444 A1 | 7/2009 | Wiemker et al. |
| 2009/0216112 A1 | 8/2009 | Assis et al. |
| 2009/0245601 A1 | 10/2009 | Cohen et al. |
| 2009/0257631 A1 | 10/2009 | Baumgart |
| 2009/0264752 A1 | 10/2009 | Markowitz et al. |
| 2009/0264753 A1 | 10/2009 | Von Schulthess |
| 2009/0275831 A1 | 11/2009 | Hall |
| 2009/0281418 A1 | 11/2009 | Ruijters et al. |
| 2009/0299195 A1 | 12/2009 | Muller et al. |
| 2009/0304593 A1* | 12/2009 | Frinking et al. ............... 424/9.1 |
| 2009/0306547 A1 | 12/2009 | Iddan et al. |
| 2010/0041949 A1 | 2/2010 | Tolkowsky |
| 2010/0049034 A1 | 2/2010 | Eck et al. |
| 2010/0054573 A1 | 3/2010 | Shekhara |
| 2010/0067768 A1 | 3/2010 | Ionasec et al. |
| 2010/0094124 A1 | 4/2010 | Schoonenberg et al. |
| 2010/0094127 A1 | 4/2010 | Xu |
| 2010/0099979 A1 | 4/2010 | Schoonenberg et al. |
| 2010/0111396 A1 | 5/2010 | Boucheron |
| 2010/0114289 A1 | 5/2010 | Camus |
| 2010/0123715 A1 | 5/2010 | Hansegard |
| 2010/0134517 A1 | 6/2010 | Saikaly et al. |
| 2010/0135546 A1 | 6/2010 | Cziria |
| 2010/0157041 A1 | 6/2010 | Klaiman et al. |
| 2010/0160764 A1 | 6/2010 | Steinberg et al. |
| 2010/0160773 A1 | 6/2010 | Cohen et al. |
| 2010/0161022 A1 | 6/2010 | Tolkowsky |
| 2010/0161023 A1 | 6/2010 | Cohen et al. |
| 2010/0171819 A1 | 7/2010 | Tolkowsky et al. |
| 2010/0172556 A1 | 7/2010 | Cohen et al. |
| 2010/0174192 A1 | 7/2010 | Azuma |
| 2010/0191102 A1 | 7/2010 | Steinberg et al. |
| 2010/0198063 A1 | 8/2010 | Huber |
| 2010/0220917 A1 | 9/2010 | Steinberg et al. |
| 2010/0222671 A1 | 9/2010 | Cohen et al. |
| 2010/0228076 A1 | 9/2010 | Blank et al. |
| 2010/0246910 A1 | 9/2010 | Wiemker |
| 2010/0272340 A1* | 10/2010 | Bar-Aviv et al. ............... 382/131 |
| 2010/0290693 A1 | 11/2010 | Cohen et al. |
| 2010/0310140 A1 | 12/2010 | Schneider |
| 2010/0312100 A1 | 12/2010 | Zarkh et al. |
| 2010/0318115 A1 | 12/2010 | Chanduszko et al. |
| 2010/0331670 A1 | 12/2010 | Strommer et al. |
| 2011/0015520 A1 | 1/2011 | Meetz et al. |
| 2011/0026786 A1 | 2/2011 | Mohamed |
| 2011/0033094 A1 | 2/2011 | Zarkh |
| 2011/0034801 A1 | 2/2011 | Baumgart |
| 2011/0052030 A1 | 3/2011 | Bruder et al. |
| 2011/0071404 A1 | 3/2011 | Schmidtt et al. |
| 2011/0075912 A1 | 3/2011 | Rieber et al. |
| 2011/0087104 A1 | 4/2011 | Moore |
| 2011/0112398 A1 | 5/2011 | Zarkh et al. |
| 2011/0118825 A1 | 5/2011 | Hunter et al. |
| 2011/0157154 A1 | 6/2011 | Bernard et al. |
| 2011/0228992 A1 | 9/2011 | Wels et al. |
| 2011/0230758 A1 | 9/2011 | Eichler |
| 2011/0235889 A1* | 9/2011 | Spahn ............... 382/132 |
| 2011/0286627 A1 | 11/2011 | Takacs et al. |
| 2011/0293163 A1 | 12/2011 | Kargar et al. |
| 2011/0319752 A1 | 12/2011 | Steinberg et al. |
| 2012/0004529 A1 | 1/2012 | Tolkowsky et al. |
| 2012/0004533 A1 | 1/2012 | Peng |
| 2012/0004537 A1 | 1/2012 | Tolkowsky et al. |
| 2012/0014574 A1 | 1/2012 | Ferschel et al. |
| 2012/0029339 A1 | 2/2012 | Cohen et al. |
| 2012/0051606 A1 | 3/2012 | Saikia |
| 2012/0059220 A1 | 3/2012 | Holsing |
| 2012/0059253 A1 | 3/2012 | Wang et al. |
| 2012/0065507 A1 | 3/2012 | Brunke |
| 2012/0069167 A1 | 3/2012 | Liu et al. |
| 2012/0072190 A1 | 3/2012 | Sharma et al. |
| 2012/0083696 A1 | 4/2012 | Kitamura |
| 2012/0093379 A1* | 4/2012 | Florent et al. ............... 382/131 |
| 2012/0123238 A1 | 5/2012 | Vaillant et al. |
| 2012/0130242 A1 | 5/2012 | Burgess |
| 2012/0140998 A1 | 6/2012 | Zhu |
| 2012/0207367 A1 | 8/2012 | Kneepkens |
| 2012/0215093 A1 | 8/2012 | Ji |
| 2012/0224751 A1 | 9/2012 | Kemp |
| 2012/0230565 A1 | 9/2012 | Steinberg et al. |
| 2012/0245460 A1 | 9/2012 | Slomka |
| 2012/0250974 A1* | 10/2012 | Miyamoto ............... 382/132 |
| 2012/0294498 A1 | 11/2012 | Popovic |
| 2012/0300981 A1 | 11/2012 | Yeh et al. |
| 2012/0310081 A1 | 12/2012 | Adler et al. |
| 2013/0004044 A1 | 1/2013 | Ross |
| 2013/0030295 A1 | 1/2013 | Huennekens |
| 2013/0046167 A1 | 2/2013 | Shah |
| 2013/0053664 A1 | 2/2013 | Jian et al. |
| 2013/0109958 A1 | 5/2013 | Baumgart |
| 2013/0109959 A1 | 5/2013 | Baumgart |
| 2013/0116739 A1 | 5/2013 | Brada et al. |
| 2013/0120296 A1 | 5/2013 | Merritt |
| 2013/0120297 A1 | 5/2013 | Merritt |
| 2013/0123616 A1 | 5/2013 | Merritt |
| 2013/0308844 A1 | 11/2013 | Florent et al. |
| 2013/0329030 A1 | 12/2013 | Tolkowsky et al. |
| 2013/0329977 A1 | 12/2013 | Tolkowsky et al. |
| 2014/0094660 A1 | 4/2014 | Tolkowsky et al. |
| 2014/0094689 A1 | 4/2014 | Cohen et al. |
| 2014/0094690 A1 | 4/2014 | Tolkowsky et al. |
| 2014/0094691 A1 | 4/2014 | Steinberg et al. |
| 2014/0094692 A1 | 4/2014 | Tolkowsky et al. |
| 2014/0094693 A1 | 4/2014 | Cohen et al. |
| 2014/0100451 A1 | 4/2014 | Tolkowsky et al. |

(56) References Cited

U.S. PATENT DOCUMENTS

| | | |
|---|---|---|
| 2014/0107479 A1 | 4/2014 | Klaiman et al. |
| 2014/0111541 A1 | 4/2014 | Tolkowsky et al. |
| 2014/0112566 A1 | 4/2014 | Steinberg et al. |
| 2014/0114184 A1 | 4/2014 | Klaiman et al. |
| 2014/0114185 A1 | 4/2014 | Tolkowsky et al. |
| 2014/0114308 A1 | 4/2014 | Tolkowsky et al. |
| 2014/0114333 A1 | 4/2014 | Tolkowsky et al. |
| 2014/0121513 A1 | 5/2014 | Tolkowsky et al. |
| 2015/0282737 A1 | 10/2015 | Tolkowsky et al. |
| 2015/0282889 A1 | 10/2015 | Cohen et al. |
| 2015/0282890 A1 | 10/2015 | Cohen et al. |
| 2015/0283319 A1 | 10/2015 | Tolkowsky et al. |

FOREIGN PATENT DOCUMENTS

| | | |
|---|---|---|
| WO | 99/07354 A2 | 2/1999 |
| WO | 00/33755 A1 | 6/2000 |
| WO | 01/10313 A1 | 2/2001 |
| WO | 01/43642 | 6/2001 |
| WO | 03/043516 A2 | 5/2003 |
| WO | 03/096894 | 11/2003 |
| WO | 2005/026891 | 3/2005 |
| WO | 2005/051452 A2 | 6/2005 |
| WO | 2005/124689 | 12/2005 |
| WO | 2006/027781 A2 | 3/2006 |
| WO | 2006/066122 | 6/2006 |
| WO | 2006/066124 | 6/2006 |
| WO | 2006/076409 A2 | 7/2006 |
| WO | 2006/114721 A2 | 11/2006 |
| WO | 2006/121984 | 11/2006 |
| WO | 2007/002685 A2 | 1/2007 |
| WO | 2007/014028 A1 | 2/2007 |
| WO | 2007/015199 A2 | 2/2007 |
| WO | 2008/007350 A1 | 1/2008 |
| WO | 2008/062358 A1 | 5/2008 |
| WO | 2008/107905 | 9/2008 |
| WO | 2009/153794 | 12/2009 |
| WO | 2010/058398 A2 | 5/2010 |
| WO | 2011/046903 A2 | 4/2011 |
| WO | 2011/046904 A1 | 4/2011 |
| WO | 2011128797 A1 | 10/2011 |
| WO | 2011/145094 A2 | 11/2011 |
| WO | 2012/014212 A1 | 2/2012 |
| WO | 2012/028190 A1 | 3/2012 |
| WO | 2012095755 A1 | 7/2012 |
| WO | 2012107857 A1 | 8/2012 |
| WO | 2012/138872 A2 | 10/2012 |
| WO | 2012/138874 A2 | 10/2012 |
| WO | 2012/176191 A1 | 12/2012 |
| WO | 2013/025602 A1 | 2/2013 |
| WO | 2013061225 A1 | 5/2013 |
| WO | 2013/084345 A1 | 6/2013 |
| WO | 2013/128233 A1 | 9/2013 |
| WO | 2013/169814 A1 | 11/2013 |
| WO | 2013/175472 A2 | 11/2013 |
| WO | 2014/002095 A2 | 1/2014 |
| WO | 2015/155770 A1 | 10/2015 |

OTHER PUBLICATIONS

Communication dated Oct. 24, 2014 from the USPTO in U.S. Appl. No. 12/650,121.
Communication dated Aug. 29, 2014 from the USPTO in U.S. Appl. No. 14/098,140.
Communication dated Nov. 7, 2014 from the USPTO in U.S. Appl. No. 14/096,968.
Communication dated Sep. 5, 2014 from the USPTO in U.S. Appl. No. 14/143,430.
Communication dated Sep. 11, 2014 from the USPTO in U.S. Appl. No. 12/650,152.
Communication dated Oct. 15, 2014 from the USPTO in U.S. Appl. No. 12/781,366.
Communication dated Oct. 8, 2014 from the USPTO in U.S. Appl. No. 14/098,093.
Communication dated Oct. 14, 2014 from the USPTO in U.S. Appl. No. 12/075,252.
Boyle et al., entitled "Assessment of a Novel Angiographic Image Stabilization System for Percutaneous Coronary Intervention" (Journal of Interventional Cardiology, vol. 20 No. 2, 2007.
Timinger et al., entitled "Motion compensated coronary interventional navigation by means of diaphragm tracking and elastic motion models" (Phys Med Biol. Feb. 7, 2005;50(3):491-503.
Timinger et al., entitled "Motion compensation for interventional navigation on 3D static roadmaps based on an affine model and gating" (Phys Med Biol. Mar. 7, 2004;49(5):719-32.
Turski et al., entitled "Digital Subtraction Angiography 'Road Map'" (American Journal of Roentgenology, 1982.
Iddan et al., entitled "3D imaging in the studio and elsewhere" (SPIE Proceedings vol. 4298, 2001.
"Catheter Insertion Simulation with Combined Visual and Haptic Feedback," by Zorcolo et al. (Center for Advanced Studies, Research and Development in Sardinia).
"4D-CT imaging of a volume influenced by respiratory motion on multi-slice CT Tinsu Pan," by Lee et al., (Medical Physics, Feb. 2004, vol. 31, Issue 2, pp. 333-340)—an abstract.
"New 4-D imaging for real-time intraoperative MRI: adaptive 4-D scan," by Tokuda et al. (Med Image Comput Assist Intent Int Conf. 2006;9(Pt 1):454-61) an abstract.
"Real-time interactive viewing of 4D kinematic MR joint studies," by Schulz et al. (Med Image Comput Assist Intent Int Conf. 2005;8(Pt 1):467-73.)—an abstract.
"4D smoothing of gated SPECT images using a left-ventricle shape model and a deformable mesh," by Brankov et al., (Nuclear Science Symposium Conference Record, 2004 IEEE, Oct. 2004, vol. 5, 2845-2848).
"Prospective motion correction of X-ray images for coronary interventions," by Shechter et al. (IEEE Trans Med Imaging. Apr. 2005;24(4):441-50).
"Cardiac Imaging: We Got the Beat!" by Elizabeth Morgan (Medical Imaging, Mar. 2005).
"Noninvasive Coronary Angiography by Retrospectively ECG-Gated Multislice Spiral CT," by Achenbach et al., (Circulation. Dec. 5, 2000;102(23):2823-8).
"Spatially-adaptive temporal smoothing for reconstruction of dynamic and gated image sequences," by Brankov et al., (Nuclear Science Symposium Conference Record, 2000 IEEE, 2000, vol. 2, 15/146-15/150)—an abstract.
"Full-scale clinical implementation of a video based respiratory gating system," by Ramsey et al., (Engineering in Medicine and Biology Society, 2000. Proceedings of the 22nd Annual International Conference of the IEEE, 2000, vol. 3, 2141-2144)—an abstract.
"Three-Dimensional Respiratory-Gated MR Angiography of the Coronary Arteries: Comparison with Conventional Coronary Angiography," by Post et al., (AJR, 1996; 166: 1399-1404).
Soffie Mansson, et al., "Dosimetric verification of breathing adapted radiotherapy using polymer gel", Journal of Physics: Conference series 56 (200) 300-303.
"From 2D to 4D" AXIOM Innovations— Mar. 2008, www.siemens.com/healthcare-magazine.
A Brochure: Impella® 2.5, Percutaneous Circulatory Support System, ABIOMED™, 2007.
Frangi et al., entitled "Multiscale vessel enhancement filtering" (Medical Image Computing and Computer Assisted Intervention—MICCAI 1998—Lecture Notes in Computer Science, vol. 1496, Springer Verlag, Berlin, Germany, pp. 130-137).
Dijkstra, entitled "A Note on Two Problems in Connexion with Graphs" (Numerische Mathematik I, 269-271, 1959).
Zarkh et al., entitled "Guide wire navigation and therapeutic device localization for catheterization procedure" (International Congress Series 1281 (2005) 311-316.
Brochure: At the Transvascular Cardiovascular Therapeutics (TCT) conference held in Washington DC, USA in Oct. 2008, Paieon Inc. demonstrated the CardiOp-THV system for real-time navigation and positioning of a trans-catheter heart valve.

(56) References Cited

OTHER PUBLICATIONS

Brochure: At the TCT conference held in San Francisco, USA in Sep. 2009, Paieon Inc. demonstrated the IC-PRO Comprehensive Imaging Workstation for providing assistance in cardiac catheterization procedures.
An International Search Report dated Sep. 8, 2009, which issued during the prosecution of Applicant's PCT/IL09/00610.
An International Search Report dated Jan. 15, 2009, issued during the prosecution of Applicant's PCT Patent Application No. PCT/IL08/000316.
An International Search Report dated May 19 2010 issued during the prosecution of Applicant's PCT Patent Application No. PCT/IL2009/001089.
"A new point matching algorithm for non-rigid registration," by Chui (Computer Vision and Image Understanding 89 (2003) 114-141).
"Advanced and Challenges in Super-Resolution," by Farsiu (International Journal of Imaging Systems and Technology, vol. 14, No. 2, pp. 47-57, Special issue on high-resolution image reconstruction, Aug. 2004).
"Image Registration by Minimization of Residual Complexity," by Myronenko (CVPR 2009).
"Image inpainting," by Bertalmio (ACM Siggraph 2000, New Orleans, Louisiana, USA, Jul. 2000).
"Nonrigid registration using free-form deformations: application to breast MR images," by Rueckert, (IEEE Trans. Med. Img, vol. 18, No. 8, 1999).
"Unwarping of unidirectionally distorted EPI images," by Kybic (IEEE Trans. Med. Img., vol. 19, No. 2, 2000).
"Geometrically Correct 3-D Reconstruction of Intravascular Ultrasound Images by Fusion with Biplane Angiography—Methods and Validation," Andreas Wahle, IEEE Transactions on Medical Imaging, Final Manuscript #187/98, June 30, 1999.
An International Search Report dated Jan. 6, 2012, which issued during the prosecution of Applicant's PCT Application No. PCT/IL11/00391.
An Official Action dated Nov. 28, 2011, which issued during the prosecution of Applicant's U.S. Appl. No. 12/075,252.
An Official Action dated Dec. 8, 2011, which issued during the prosecution of Applicant's U.S. Appl. No. 12/075,244.
U.S. Appl. No. 60/845,347 to Strommer et al., filed Sep. 2006.
International Search Report dated Mar. 2, 2012, issued in PCT/IL11/00612.
Office Action dated Mar. 14, 2012, issued in U.S. Appl. No. 12/075,214.
Office Action dated Mar. 15, 2012, issued in U.S. Appl. No. 12/649,944.
Office Action dated Mar. 15, 2012, issued in U.S. Appl. No. 12/650,152.
Office Action dated May 22, 2012, issued in U.S. Appl. No. 12/075,244.
Umeda, H. et al., "Promising efficacy of primary gradual and prolonged balloon angioplasty in small coronary arteries: A randomized comparison with cutting balloon angioplasty and conventional balloon angioplasty", 2004.
W. Santamore et al., "A microcomputer based automated quantative coronary angiographic analysis system," Annals of Biomedical Engineering, vol. 16, pp. 367-377, 1988.
V. Duddalwar, "Multislice CT angiography: a practical guide to CT angiography in vascular imaging and intervention," the British Journal of Radiology, 77 (2004), S27-S38.
Official Action dated Oct. 23, 2012, which issued during the prosecution of JP Application No. 2009-552328.
Official Action dated Nov. 23, 2012, which issued during the prosecution of U.S. Appl. No. 12/649,944.
Official Action dated Aug. 27, 2012, which issued during the prosecution U.S. Appl. No. 12/075,214.
International Search Report dated Oct. 10 2012, which issued during the prosecution of PCT/IL2012/000246.
Communication dated Sep. 5, 2012, which issued during the prosecution of EP Application 09 766 329.8-1526.
Communication dated Oct. 29, 2012, which issued during the prosecution of EP Application 08 719941.0-1265/2129284.
Computer translation of JP 2010-253017 to Takeshi.
G. Mancini et al., "Automated quantitative coronary arteriography: morphologic and physiologic validation in vivo of a rapid digital angiographic method," Circulation 1987;75:452-460.
I. Kompatsiaris et al., "Deformable Boundary Detection of Stents in Angiographic Images," IEEE Transactions on Medical Imaging, vol. 19, No. 6, June 2000.
L. Yaneza et al., " Atherosclerotic Plaque Can Be Quantified Using Multifractal and Wavelet Decomposition Techniques," Abstracts—Angiography & Interventional Cardiology, JACC Mar. 3, 2004.
Official Action dated Oct. 31, 2012, which issued during the prosecution U.S. Appl. No. 12/075,244.
Official Action dated Sep. 20, 2012, which issued during the prosecution of U.S. Appl. No. 12/649,955.
U.S. Appl. No. 61/359,431.
W. Goodman et al., "Coronary-Artery Calcification in Young Adults With End-Stage Renal Disease Who Are Undergoing Dialysis," The New England Journal of Medicine, vol. 342 No. 20.
W. Leung et al., "Coronary Artery Quantitation and Data Management System for Paired Cineangiograms," Catheterization and Cardiovascular Diagnosis 24:121-134 (1991).
A search report dated Nov. 23, 2012, which issued during the prosecution of Applicant's EP Application 09 827264.4-1265/2358269.
An examination report dated Dec. 5, 2012, which issued during the prosecution of Applicant's EP Application 09766329.8.
An Official Action dated Dec. 10, 2012, which issued during the prosecution of Applicant's U.S. Appl. No. 12/650,156.
An Official Action dated Dec. 11, 2012, which issued during the prosecution of Applicant's U.S. Appl. No. 12/650,152.
An Official Action dated Jan. 22, 2013, which issued during the prosecution of Applicant's U.S. Appl. No. 12/650,121.
An Official Action dated Jan. 28, 2013, which issued during the prosecution of Applicant's U.S. Appl. No. 12/781,366.
An Official Action dated Feb. 4, 2013, which issued during the prosecution of Applicant's U.S. Appl. No. 13/228,185.
Peng Wang et al.: "Image-Based Device Tracking for the Co-registration of Angiography and Intravascular Ultrasound Images", MICCAI 2011, Part I, LINCS 6891, pp. 161-168, 2011.
An Official Action dated Jul. 2, 2013, which issued during the prosecution of Applicant's U.S. Appl. No. 12/075,244.
An Official Action dated Jun. 19, 2013, which issued during the prosecution of Applicant's U.S. Appl. No. 12/075,214.
An Official Action dated May 31, 2013, which issued during the prosecution of Applicant's U.S. Appl. No. 12/075,252.
An Official Action dated May 6, 2013, which issued during the prosecution of Applicant's U.S. Appl. No. 12/487,315.
A Notice of Allowance dated Jun. 4, 2013, which issued in Applicant's U.S. Appl. No. 12/649,960.
An Official Action dated Sep. 6, 2013, which issued during the prosecution of Applicant's U.S. Appl. No. 12/650,605.
An Official Action dated Aug. 30, 2013, which issued during the prosecution of Applicant's U.S. Appl. No. 12/650,121.
An Official Action dated Sep. 12, 2013, which issued during the prosecution of Applicant's U.S. Appl. No. 12/781,260.
A Notice of Allowance in Applicant's U.S. Appl. No. 12/781,414.
An Official Action dated Aug. 3, 2012, which issued during the prosecution of Applicant's U.S. Appl. No. 12/781,294.
An Official Action dated Jun. 19, 2012, which issued during the prosecution of Applicant's U.S. Appl. No. 12/075,252.
An Official Action dated Jun. 18, 2012, which issued during the prosecution of Applicant's U.S. Appl. No. 12/781,366.
An Official Action dated Jun. 7, 2012, which issued during the prosecution of Applicant's U.S. Appl. No. 12/650,156.
An Official Action dated May 29, 2012, which issued during the prosecution of Applicant's U.S. Appl. No. 12/650,121.
Buddy D. Ratner, "Biomaterials Science: An Introduction to Materials in Medicine", Elsevier, chapter 7, 1996.
Gerald E. Miller, "Fundamentals of Biomedical Transport Processes, Morgan & Claypool Publishers", chapter 2, 2010.

(56) References Cited

OTHER PUBLICATIONS

Gerhard Albert ten Brinke, "Automated coronary flow reserve assessment using planar x-ray angiography", PhD dissertation, Universiteit Twente, 2011.
Jerry T. Wong et al., "Quantification of fractional flow reserve based on angiographic image data", Int J Cardiovasc Imaging 28:13-22, Jan. 7, 2011.
Kassab, G. S. et al., "Cross-sectional area and vol. compliance of porcine left coronary arteries," Am. J. Physiol. Heart Circ. Physiol. 281, H623-H628, Aug. 2011.
Molloi S. et al., "Absolute volumetric coronary blood flow measurement with digital subtraction angiography". Int J Card Imaging 14:137-145, 1998.
Molloi, S. et al., "Estimation of coronary artery hyperemic blood flow based on arterial lumen volume using angiographic images," The International Journal of Cardiovascular Imaging, vol. 28, No. 1, 1-11, Jan. 7, 2011.
Molloi, S. et al., "Quantification of coronary artery lumen volume by digital angiography: in vivo validation," Circulation 104, 2351-2357, Nov. 6, 2001.
Molloi, S. et al., "Quantification of volumetric coronary blood flow with dual-energy digital subtraction angiography," Circulation 93, 1919-1927, May 15, 1996.
Molloi, S. et al., "Regional volumetric coronary blood flow measurement by digital angiography: in vivo validation," Acad. Radiol. 11, 7, 757-766, Jul. 2004.
Sian Sen et al., "Development and Validation of a New, Adenosine-Independent Index of Stenosis Severity From Coronary Wave-Intensity Analysis". Journal of the American College of Cardiology, vol. 59, Apr. 10, 2012.
Yunlong Huo et al., "A validated predictive model of coronary fractional flow reserve," J. R. Soc. Interface, Nov. 23, 2011.
A Notice of Allowance issued in Applicant's U.S. Appl. No. 13/965,893.
An Official Action dated Nov. 13, 2013, which issued during the prosecution of Applicant's U.S. Appl. No. 12/666,879.
An Official Action dated Oct. 2, 2013, which issued during the prosecution of Applicant's U.S. Appl. No. 13/228,211.
An Official Action dated Oct. 21, 2013, which issued during the prosecution of Applicant's U.S. Appl. No. 12/075,214.
An Official Action dated Oct. 23, 2013, which issued during the prosecution of Applicant's U.S. Appl. No. 12/648,913.
An Official Action dated Oct. 25, 2013, which issued during the prosecution of Applicant's U.S. Appl. No. 12/781,366.
An Official Action dated Oct. 3, 2013, which issued during the prosecution of Applicant's U.S. Appl. No. 13/228,185.
An Official Action dated Oct. 30, 2013, which issued during the prosecution of Applicant's U.S. Appl. No. 13/228,335.
An Official Action dated Oct. 4, 2013, which issued during the prosecution of Applicant's U.S. Appl. No. 12/649,955.
Correspondence from the International Searching Authority in Applicant's PCT/IL13/50549.
Correspondence from the International Searching Authority in Applicant's PCT/IL2013/050438.
International Search Report and Written Opinion for International Patent Application PCT/IL2013/050438 mailed Dec. 2, 2013.
Office Action, dated Jan. 7, 2014, issued by the United States Patent and Trademark Office, in counterpart U.S. Appl. No. 12/075,244.
Office Action, dated Feb. 12, 2014, issued by the United States Patent and Trademark Office, in counterpart U.S. Appl. No. 12/781,260.
Office Action, dated Dec. 31, 2013, issued by the United States Patent and Trademark Office, in counterpart U.S. Appl. No. 12/075,252.
Notice of Allowance, dated Jan. 3, 2014, issued by the United States Patent and Trademark Office, in counterpart U.S. Appl. No. 13/965,872.
Search Report, dated Jan. 22, 2014, issued by the International Searching Authority, in counterpart Application No. PCT/IL13/50549.
Written Opinion, dated Jan. 22, 2014, issued by the International Searching Authority, in counterpart Application No. PCT/IL13/50549.
An Official Action dated Feb. 20, 2014, which issued during the prosecution of Applicant's U.S. Appl. No. 12/075,214.
An Official Action dated May 6, 2014, which issued during the prosecution of Applicant's U.S. Appl. No. 12/075,252.
A Notice of Allowance issued in Applicant's U.S. Appl. No. 12/666,879.
An Official Action dated Mar. 21, 2014, which issued during the prosecution of Applicant's U.S. Appl. No. 12/648,913.
An Official Action dated Apr. 3, 2014, which issued during the prosecution of Applicant's U.S. Appl. No. 12/649,955.
An Official Action dated Mar. 14, 2014, which issued during the prosecution of Applicant's U.S. Appl. No. 12/650,605.
An Official Action dated Apr. 25, 2014, which issued during the prosecution of Applicant's U.S. Appl. No. 12/650,121.
An Official Action dated Apr. 24, 2014, which issued during the prosecution of Applicant's U.S. Appl. No. 12/781,366.
An Official Action dated Apr. 17, 2014, which issued during the prosecution of Applicant's U.S. Appl. No. 13/228,211.
An Official Action dated Apr. 28, 2014, which issued during the prosecution of Applicant's U.S. Appl. No. 13/228,185.
An Official Action dated May 5, 2014, which issued during the prosecution of Applicant's U.S. Appl. No. 14/096,968.
An Official Action dated Feb. 14, 2014, which issued during the prosecution of Applicant's U.S. Appl. No. 14/098,140.
Pyxaras et al., "Quantitative angiography optical coherence tomography for the functional assessment of nonobstructive coronary stenoses" (Medscape), Oct. 2013, 11 pages total.
Tu et al., "In vivo comparison of arterial lumen dimensions assessed by co-registered 3D quantitative coronary angiography intravascular ultrasound and optical coherence tomography.", Int J Cardiovasc Imaging (2012) 28:1315-1327, Jan. 20, 2012, DOI 10.1007/s10554-012-0016-6, 13 pages total.
Tu et al, "Fusion of 3D QCA and IVUS/OCT", Int J Cardiovasc Imaging (2011) 27:197-207, Jan. 25, 2011, DOI 10.1007/s10554-011-9809-2, 11 pages total.
Communication dated Mar. 25, 2015 from the United States Patent and Trademark Office in counterpart U.S. Appl. No. 12/075,252.
Communication dated Apr. 13, 2015 from the United States Patent and Trademark Office in counterpart U.S. Appl. No. 12/649,944.
Communication dated Apr. 22, 2015 from the United States Patent and Trademark Office in counterpart U.S. Appl. No. 14/142,082.
Communication dated Apr. 10, 2015 from the United States Patent and Trademark Office in counterpart U.S. Appl. No. 12/648,913.
Communication dated Apr. 10, 2015 from the United States Patent and Trademark Office in counterpart U.S. Appl. No. 12/650,152.
Communication dated Mar. 16, 2015 from the United States Patent and Trademark Office in counterpart U.S. Appl. No. 13/228,211.
Communication dated Mar. 23, 2015 from the United States Patent and Trademark Office in counterpart U.S. Appl. No. 14/097,922.
Communication dated Mar. 16, 2015 from the United States Patent and Trademark Office in counterpart U.S. Appl. No. 13/228,185.
Communication dated Feb. 23, 2015 from the United States Patent and Trademark Office in counterpart U.S. Appl. No. 14/143,184.
Communication dated May 6, 2015 from the United States Patent and Trademark Office in counterpart U.S. Appl. No. 12/781,260.
Communication dated May 11, 2015 from the United States Patent and Trademark Office in counterpart U.S. Appl. No. 12/650,605.
Communication dated May 12, 2015 from the Japanese Patent Office in counterpart application No. 521284/2013.
A Notice of Allowance dated Jun. 24, 2014, issued in Applicant's U.S. Appl. No. 14/097,603.
An Official Action dated Jul. 3, 2014, which issued during the prosecution of Applicant's U.S. Appl. No. 12/648,913.
An Official Action dated Jul. 30, 2014, which issued during the prosecution of Applicant's U.S. Appl. No. 12/075,214.
An Official Action dated Jul. 31, 2014, which issued during the prosecution of Applicant's U.S. Appl. No. 12/649,944.
An Official Action dated Jun. 18, 2014, which issued during the prosecution of Applicant's U.S. Appl. No. 12/075,244.

(56) References Cited

OTHER PUBLICATIONS

An Official Action dated May 21, 2014, which issued during the prosecution of Applicant's U.S. Appl. No. 12/650,156.
An Official Action dated May 29, 2014, which issued during the prosecution of Applicant's U.S. Appl. No. 14/097,922.
An Official Action dated May 30, 2014, which issued during the prosecution of Applicant's U.S. Appl. No. 13/228,335.
An Official Action dated Jun. 3, 2014, which issued during the prosecution of Applicant's U.S. Appl. No. 12/781,260.
Communication dated Dec. 11, 2014, issued by the United States Patent and Trademark Office in corresponding U.S. Appl. No. 12/648,913.
Communication dated Feb. 4, 2015, issued by the United States Patent and Trademark Office in corresponding U.S. Appl. No. 12/649,955.
Communication dated Nov. 24, 2014, issued by the United States Patent and Trademark Office in corresponding U.S. Appl. No. 12/781,260.
Communication dated Jan. 6, 2015, issued by the United States Patent and Trademark Office in corresponding U.S. Appl. No. 12/650,605.
Communication dated Feb. 6, 2015, issued by the United States Patent and Trademark Office in corresponding U.S. Appl. No. 12/650,121.
Communication dated Nov. 24, 2014, issued by the United States Patent and Trademark Office in corresponding U.S. Appl. No. 12/649,944.
Communication dated Feb. 6, 2015, issued by the United States Patent and Trademark Office in corresponding U.S. Appl. No. 12/781,366.
Communication dated Jan. 16, 2015, issued by the United States Patent and Trademark Office in corresponding U.S. Appl. No. 13/228,229.
Communication dated Jan. 6, 2015, issued by the United States Patent and Trademark Office in corresponding U.S. Appl. No. 13/228,335.
Communication dated Nov. 28, 2014, issued by the United States Patent and Trademark Office in corresponding U.S. Appl. No. 14/097,922.
Communication dated Dec. 4, 2014, issued by the United States Patent and Trademark Office in corresponding U.S. Appl. No. 14/098,114.
Communication dated Nov. 24, 2014, issued by the United States Patent and Trademark Office in corresponding U.S. Appl. No. 12/650,156.
Communication dated Dec. 19, 2014, issued by the United States Patent and Trademark Office in corresponding U.S. Appl. No. 14/143,430.
Communication dated Jan. 12, 2015, issued by the United States Patent and Trademark Office in corresponding U.S. Appl. No. 14/143,289.
Communication dated Jan. 23, 2015, issued by the European Patent Office in counterpart Application No. 12802046.8.
An Official Action dated Aug. 17, 2015, which issued during the prosecution of Applicant's U.S. Appl. No. 12/648,913.
An Official Action dated Aug. 27, 2015, which issued during the prosecution of Applicant's U.S. Appl. No. 12/650,121.
An Official Action dated Oct. 22, 2015, which issued during the prosecution of Applicant's U.S. Appl. No. 12/649,944.
An Official Action dated Sep. 11, 2015, which issued during the prosecution of Applicant's U.S. Appl. No. 12/781,260.
An Official Action dated Sep. 21, 2015, which issued during the prosecution of Applicant's U.S. Appl. No. 13/228,229.
An Official Action dated Sep. 3, 2015, which issued during the prosecution of Applicant's U.S. Appl. No. 13/228,211.
An Official Action dated Oct. 7, 2015, which issued during the prosecution of Applicant's U.S. Appl. No. 13/228,185.
An Official Action dated Aug. 11, 2015, which issued during the prosecution of Applicant's U.S. Appl. No. 13/228,335.
An Official Action dated Aug. 12, 2015, which issued during the prosecution of Applicant's U.S. Appl. No. 14/097,922.
An Official Action dated Oct. 7, 2015, which issued during the prosecution of Applicant's U.S. Appl. No. 14/142,082.
An Official Action dated Aug. 25, 2015, which issued during the prosecution of Applicant's U.S. Appl. No. 14/143,184.
An Official Action dated Sep. 23, 2015, which issued during the prosecution of Applicant's U.S. Appl. No. 14/742,996.
A European Patent report dated Sep. 8, 2015, which issued during the prosecution of Applicant's European Patent Application No. 08719941.0.
An Official Action dated Sep. 4, 2015, which issued during the prosecution of Applicant's Canadian Application No. 2,874,415.
An International Search Report and Written Opinion dated Aug. 25, 2015, which issued during prosecution of Applicant's PCT/IL2015/050372.
An Official Action dated Jul. 28, 2015, which issued during the prosecution of Applicant's U.S. Appl. No. 12/075,252.
An Official Action dated Jul. 6, 2015, which issued during the prosecution of Applicant's U.S. Appl. No. 12/649,955.
An Official Action dated May 19, 2015 which issued during the prosecution of Applicant's U.S. Appl. No. 13/228,229.
An Official Action dated May 21, 2015, which issued during the prosecution of Applicant's U.S. Appl. No. 14/098,140.
An Official Action dated May 21, 2015, which issued during the prosecution of Applicant's Canadian Application No. 2,874,415.
An Official Action dated Jul. 2, 2015, which issued during the prosecution of Applicant's Canadian Application No. 2,875,346.
An English-translation of an Official Action dated Jun. 23, 2015, which issued during the prosecution of Applicant's JP Application No. 2014-164417.

* cited by examiner

LUMINAL BACKGROUND CLEANING

CROSS REFERENCES TO RELATED APPLICATIONS

The present application is a U.S. national phase of PCT Application no. PCT/IL2012/000246 to Barzelay (published as WO 12/176191), filed Jun. 21, 2012, which claims priority from U.S. Provisional Patent Application 61/457,866 to Barzelay, filed Jun. 23, 2011.

The present application is related to International Patent Application PCT/IL2011/000612 (published as WO 12/014,212), entitled "Co-use of endoluminal data and extraluminal imaging," filed Jul. 28, 2011, which:

(a) claims the benefit of:

U.S. Provisional Patent Application 61/344,464, entitled "Co-use of endoluminal data and extraluminal imaging," filed 29 Jul. 2010;

U.S. Provisional Patent Application 61/344,875, entitled "Co-use of endoluminal data and extraluminal imaging," filed 1 Nov. 2010;

U.S. Provisional Patent Application 61/457,339, entitled "Co-use of endoluminal data and extraluminal imaging," filed 3 Mar. 2011;

U.S. Provisional Patent Application 61/457,455, entitled "Co-use of endoluminal data and extraluminal imaging," filed 1 Apr. 2011;

U.S. Provisional Patent Application 61/457,780, entitled "Co-use of endoluminal data and extraluminal imaging," filed 2 Jun. 2011; and U.S. Provisional Patent Application 61/457,951, entitled "Co-use of endoluminal data and extraluminal imaging," filed 15 Jul. 2011; and (b) is a continuation-in-part of U.S. patent application Ser. No. 12/650,605 to Cohen (published as US 2010/0172556), filed Dec. 31, 2009, which:

(i) is a continuation of U.S. patent application Ser. No. 12/666,879 to Steinberg (issued as U.S. Pat. No. 8,781,193), which is the US national phase of PCT Application No. PCT/IL2009/001089 to Cohen (published as WO 10/058,398), filed Nov. 18, 2009, which claims priority from the following patent applications:

U.S. Provisional Patent Application 61/193,329, entitled "Apparatuses and methods for the automatic generation of a road map from angiographic images of a cyclically-moving organ," to Steinberg, filed Nov. 18, 2008

U.S. Provisional Patent Application 61/193,915, entitled "Image processing and tool actuation for medical procedures," to Steinberg, filed Jan. 8, 2009

U.S. Provisional Patent Application 61/202,181, entitled "Image processing and tool actuation for medical procedures," to Steinberg, filed Feb. 4, 2009

U.S. Provisional Patent Application 61/202,451, entitled "Image processing and tool actuation for medical procedures," to Steinberg, filed Mar. 2, 2009

U.S. Provisional Patent Application 61/213,216, entitled "Image processing and tool actuation for medical procedures," to Steinberg, filed May 18, 2009

U.S. Provisional Patent Application 61/213,534, entitled "Image Processing and Tool Actuation for Medical Procedures," to Steinberg, filed Jun. 17, 2009

U.S. Provisional Patent Application 61/272,210, entitled "Image processing and tool actuation for medical procedures," to Steinberg, filed Sep. 1, 2009 and U.S. Provisional Patent Application 61/272,356, entitled "Image Processing and Tool Actuation for Medical Procedures" to Steinberg, filed Sep. 16, 2009; and (ii) is a continuation-in-part of U.S. patent application Ser. No. 12/075,244 to Tolkowsky (published as US 2008/0221442, now abandoned), filed Mar. 10, 2008, entitled "Imaging for use with moving organs," which claims the benefit of U.S. Provisional Patent Application Nos.:

60/906,091 filed on Mar. 8, 2007,
60/924,609 filed on May 22, 2007,
60/929,165 filed on Jun. 15, 2007,
60/935,914 filed on Sep. 6, 2007, and
60/996,746 filed on Dec. 4, 2007, all entitled "Apparatuses and methods for performing medical procedures on cyclically-moving body organs."

The present application is related to the following patent applications:

U.S. patent application Ser. No. 12/075,214 to Iddan (published as 2008/0221439, now abandoned), filed Mar. 10, 2008, entitled "Tools for use with moving organs."

U.S. patent application Ser. No. 12/075,252 to Iddan (published as US 2008/0221440), filed Mar. 10, 2008, entitled "Imaging and tools for use with moving organs."

U.S. patent application Ser. No. 12/781,260 to Blank (published as US 2010/0228076), filed May 17, 2010, entitled "Controlled actuation and deployment of a medical device."

U.S. patent application Ser. No. 12/487,315 to Iddan (issued as U.S. Pat. No. 8,700,130), filed Jun. 18, 2009, entitled "Stepwise advancement of a medical tool," which claims the benefit of U.S. Provisional Patent Application No. 61/129,331 to Iddan, filed on Jun. 19, 2008, entitled "Stepwise advancement of a medical tool."

All of the above-mentioned applications are incorporated herein by reference.

FIELD OF EMBODIMENTS OF THE INVENTION

Applications of the present invention generally relate to medical image processing. Specifically, applications of the present invention relate to background cleaning in images of body lumens and body cavities.

BACKGROUND OF THE INVENTION

Vascular catheterizations, such as coronary catheterizations, are frequently-performed medical interventions. Such interventions are typically performed in order to diagnose the blood vessels for potential disease, and/or to treat diseased blood vessels. Typically, in order to facilitate visualization of blood vessels, the catheterization is performed under extraluminal imaging. Typically, and in order to highlight the vasculature during such imaging, a contrast agent is periodically injected into the applicable vasculature. The contrast agent typically remains in the vasculature only momentarily. During the time that the contrast agent is present in the applicable vasculature, the contrast agent typically hides, in full or in part, or obscures, devices positioned or deployed within that vasculature.

The following articles do not necessarily pertain to medical procedures or body organs, but yet serve as a useful technical background.

An article entitled "Nonlocal linear image regularization and supervised segmentation," by Gilboa and Osher (SIAM Multiscale Modeling & Simulation, volume 6, issue 2, pp. 595-630, 2007), which is incorporated herein by reference, describes how a nonlocal quadratic functional of weighted differences is examined. The weights are based on image features and represent the affinity between different pixels in the image. By prescribing different formulas for the weights, one can generalize many local and nonlocal linear de-noising algorithms, including the nonlocal means filter and the bilateral filter. In this framework one can show that continuous iterations of the generalized filter obey certain global characteristics and converge to a constant solution. The linear operator associated with the Euler-Lagrange equation of the functional is closely related to the graph Laplacian. Thus, the steepest descent for minimizing the functional as a nonlocal diffusion process may be determined. This formulation allows a convenient framework for nonlocal variational minimizations, including variational denoising, Bregman iterations and the recently-proposed inverse-scale-space. The authors demonstrate how the steepest descent flow can be used for segmentation. Following kernel based methods in machine learning, the generalized diffusion process is used to propagate sporadic initial user's information to the entire image. The process is not explicitly based on a curve length energy and thus can cope well with highly non-convex shapes and corners. Reasonable robustness to noise is achieved.

An article entitled "Nonlocal Operators with Applications to Image Processing," by Gilboa and Osher (SIAM Multiscale Modeling & Simulation, volume 7, issue 3, pp. 1005-1028, 2008), which is incorporated herein by reference, describes the use of nonlocal operators to define types of flows and functionals for image processing and other applications. The authors describe a main advantage of the technique over classical Partial-Differential-Equation-based (PDE-based) algorithms as being the ability to handle better textures and repetitive structures. This topic can be viewed as an extension of spectral graph theory and the diffusion geometry framework to functional analysis and PDE-like evolutions. Some possible applications and numerical examples of the technique are provided, as is a general framework for approximating Hamilton-Jacobi equations on arbitrary grids in high dimensions, e.g., for control theory.

An article entitled "Non-local regularization of inverse problem," by Peyre, Bougleux, and Cohenin (Lecture Notes in Computer Science, 2008, Volume 5304/2008, pp. 57-68), which is incorporated herein by reference, proposes a new framework to regularize linear inverse problems using the total variation on non-local graphs. A nonlocal graph allows adaptation of the penalization to the geometry of the underlying function to recover. A fast algorithm computes, iteratively, both the solution of the regularization process and the non-local graph adapted to this solution.

An article entitled "The split Bregman method for L1 regularized problems," by Goldstein and Osher (SIAM Journal on Imaging Sciences, Volume 2, Issue 2, pp. 323-343), which is incorporated herein by reference, notes that the class of l1-regularized optimization problems has received much attention recently because of the introduction of "compressed sensing," which allows images and signals to be reconstructed from small amounts of data. Despite this recent attention, many l1-regularized problems still remain difficult to solve, or require techniques that are very problem-specific. The authors show that Bregman iteration can be used to solve a wide variety of constrained optimization problems. Using this technique, the authors propose a "Split Bregman" method, which can solve a very broad class of l1-regularized problems.

In an article entitled "Bregmanized nonlocal regularization for reconvolution and sparse reconstruction," by Zhang, Burgery, Bresson, and Osher (SIAM Journal on Imaging Sciences, Volume 3, Issue 3, July 2010), which is incorporated herein by reference, the authors propose two algorithms based on Bregman iteration and operator splitting technique for nonlocal TV regularization problems. The convergence of the algorithms is analyzed and applications to deconvolution and sparse reconstruction are presented.

SUMMARY OF EMBODIMENTS

Some applications of the present invention are applied to medical procedures performed, in whole or in part, on or within luminal body structures or body cavities. For some applications, apparatus and methods are provided for facilitating the visualization of devices positioned or deployed within a lumen or cavity at a time when the lumen or cavity is injected with contrast agent.

It should be appreciated that while using coronary catheterization as a primary example, applications of the current invention may be applied to any medical procedure in which a medical device is positioned or deployed within a body lumen or cavity, while the lumen or cavity is injected with a substance for the purpose of better discerning that lumen or cavity by means of medical imaging. Such lumens or cavities include, without limitation, any lumen or cavity of the cardiovascular system, the gastro-intestinal tract, the respiratory tract, the urinary tract, the nasal cavities, and/or any other bodily lumen or cavity.

There is therefore provided, in accordance with some applications of the present invention, apparatus for use with an input angiogram image of a device inserted inside a portion of a body of a subject, the device including radiopaque portions thereof, the angiogram image being acquired in the presence of contrast agent within the body portion, and for use with a display, the apparatus including:
  at least one processor that includes:
    background-image-generation functionality configured to generate a background image in which a relative value is assigned to a first pixel with respect to a second pixel, at least partially based upon relative values of surroundings of the first pixel and the surroundings of the second pixel in the input image;
    cleaned-image-generation functionality configured to generate a cleaned image in which visibility of the radiopaque portions of the device is increased relative to the input image, by dividing the input image by the background image; and
    output-generation functionality configured to drive the display to display an output based upon the cleaned image.

For some applications, the background-image-generation functionality is configured to generate the background image by:
  in the background image, assigning pixel values to the first pixel and the second pixel that are more similar to one another, than the similarity of pixel values that are assigned to a third pixel and a fourth pixel,
  based upon the first pixel and the second pixel having more similar surroundings to one another in the input image, than a similarity of surroundings of the third pixel and the fourth pixel to one another in the input image.

For some applications, the background-image-generation functionality is configured to generate the background image by assigning values to the first and second pixels based upon values of the first pixel and the second pixel in the input image.

For some applications, the output-generation functionality is configured to drive the display to display the cleaned image.

For some applications:
  the input angiogram image of the device includes a plurality of input angiogram images of the device, the cleaned-image-generation functionality is configured to generate a plurality of cleaned images, the cleaned images corresponding to respective input angiogram images, and the output-generation functionality is configured to:

generate a stabilized image stream by image tracking the cleaned images with respect to each other, based upon locations of the radiopaque portions of the device in the cleaned images, and drive the display to display the stabilized image stream.

For some applications:

the input angiogram image of the device includes a plurality of input angiogram images of the device, the cleaned-image-generation functionality is configured to generate a plurality of cleaned images, the cleaned images corresponding to respective input angiogram images, and the output-generation functionality is configured to:

generate a stabilized image stream by image tracking the input images with respect to each other, based upon locations of the radiopaque portions of the device in the corresponding cleaned images, and drive the display to display the stabilized image stream.

For some applications:

the input angiogram image of the device includes a plurality of input angiogram images of the device, the cleaned-image-generation functionality is configured to generate a plurality of cleaned images, the cleaned images corresponding to respective input angiogram images, and the output-generation functionality is configured to:

generate an enhanced image frame by:

aligning the cleaned images with each other, based upon locations of the radiopaque portions of the device in the cleaned images, and generating an averaged image frame based upon the aligned images, and drive the display to display the enhanced image frame.

For some applications:

the input angiogram image of the device includes a plurality of input angiogram images of the device, the cleaned-image-generation functionality is configured to generate a plurality of cleaned images, the cleaned images corresponding to respective input angiogram images, and the output-generation functionality is configured to:

generate an enhanced image frame by:

aligning the input images with each other, based upon locations of the radiopaque portions of the device in the corresponding cleaned images, and generating an averaged image frame based upon the aligned images, and drive the display to display the enhanced image frame.

For some applications:

the portion of the subject's body includes a lumen of the subject's body, the device includes an endoluminal data-acquisition device configured to acquire endoluminal data points while the device is at respective locations within the lumen, and the output-generation functionality is configured:

based upon locations of the radiopaque portions of the device in the cleaned image, to determine that a given one of the endoluminal data points corresponds to a given location within the lumen, and to drive the display to display an output, in response to the determining.

For some applications:

the portion of the subject's body includes a lumen of the subject's body, the device includes an endoluminal data-acquisition device configured to acquire endoluminal data points while the device is at respective locations within the lumen, and the output-generation functionality is configured:

based upon locations of the radiopaque portions of the device in the cleaned image, to determine that the endoluminal device is at a given location within the lumen, and in response to the determining that the endoluminal device is at the given location within the lumen, to drive the display to display an endoluminal image of the lumen corresponding to the location.

There is further provided, in accordance with some applications of the present invention, a method for use with an input angiogram image of a device inserted inside a portion of a body of a subject, the device including radiopaque portions thereof, the angiogram image being acquired in the presence of contrast agent within the body portion, the method including:

generating, with a processor, a background image in which a relative value is assigned to a first pixel with respect to a second pixel, at least partially based upon relative values of surroundings of the first pixel and surroundings of the second pixel in the input image;

generating, with the processor, a cleaned image in which visibility of the radiopaque portions of the device is increased relative to the input image, by dividing the input image by the background image; and generating an output on a display, based upon the cleaned image.

For some applications, generating the background image includes:

in the background image, assigning pixel values to the first pixel and the second pixel that are more similar to one another, than the similarity of pixel values that are assigned to a third pixel and a fourth pixel, based upon the first pixel and the second pixel having more similar surroundings to one another in the input image, than a similarity of surroundings of the third pixel and the fourth pixel to one another in the input image.

For some applications, generating the background image further includes assigning values to the first and second pixels based upon values of the first pixel and the second pixel in the input image.

For some applications, generating the output includes displaying the cleaned image.

For some applications, the input angiogram image of the device includes a plurality of input angiogram images of the device, generating the cleaned image includes generating a plurality of cleaned images, the cleaned images corresponding to respective input angiogram images, the method further includes generating a stabilized image stream by image tracking the cleaned images with respect to each other, based upon locations of the radiopaque portions of the device in the cleaned images, and generating the output includes displaying the stabilized image stream.

For some applications, the input angiogram image of the device includes a plurality of input angiogram images of the device, generating the cleaned image includes generating a plurality of cleaned images, the cleaned images corresponding to respective input angiogram images, the method further includes generating a stabilized image stream by image tracking the input images with respect to each other, based upon locations of the radiopaque portions of the device in the corresponding cleaned images, and generating the output includes displaying the stabilized image stream.

For some applications,
the input angiogram image of the device includes a plurality of input angiogram images of the device,
generating the cleaned image includes generating a plurality of cleaned images, the cleaned images corresponding to respective input angiogram images,
the method further includes generating an enhanced image frame by:
    aligning the cleaned images with each other, based upon locations of the radiopaque portions of the device in the cleaned images, and
    generating an averaged image frame based upon the aligned cleaned images, and
generating the output includes displaying the enhanced image frame.

For some applications,
the input angiogram image of the device includes a plurality of input angiogram images of the device,
generating the cleaned image includes generating a plurality of cleaned images, the cleaned images corresponding to respective input angiogram images,
the method further includes generating an enhanced image frame by:
    aligning the input images with each other, based upon locations of the radiopaque portions of the device in the corresponding cleaned images, and
    generating an averaged image frame based upon the aligned input images, and
generating the output includes displaying the enhanced image frame.

For some applications,
the portion of the subject's body includes a lumen of the subject's body,
the device includes an endoluminal data-acquisition device configured to acquire endoluminal data points while the device is at respective locations within the lumen,
the method further includes, based upon locations of the radiopaque portions of the device in the cleaned image, determining that a given one of the endoluminal data points corresponds to a given location within the lumen, and
generating the output includes generating the output in response to the determining.

For some applications,
the portion of the subject's body includes a lumen of the subject's body,
the device includes an endoluminal device configured to be moved through the lumen,
the method further includes, based upon locations of the radiopaque portions of the device in the cleaned image, determining that the endoluminal device is at a given location within the lumen, and
generating the output includes, in response to the determining that the endoluminal device is at the given location within the lumen, generating an endoluminal image of the lumen corresponding to the location.

The present invention will be more fully understood from the following detailed description of embodiments thereof, taken together with the drawings, in which:

DETAILED DESCRIPTION OF EMBODIMENTS

Terminology

Figure 1A:
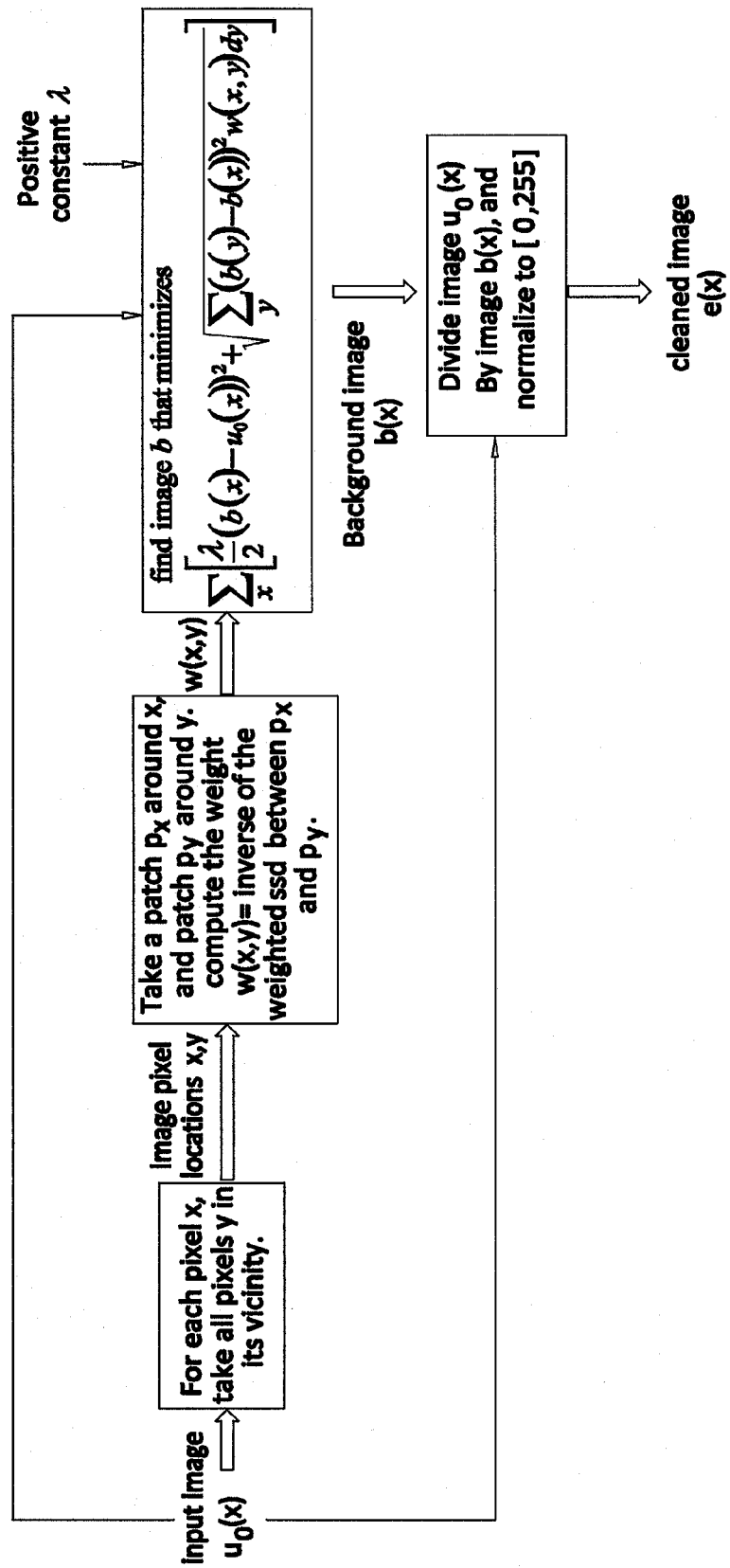
FIG. 1A is a flow chart, at least some of the steps of which are used to generate a cleaned luminal image from an input luminal image, in accordance with some applications of the present invention.

The terms "medical tool," "tool", "device," and "probe" refer to any type of a diagnostic or therapeutic or other functional tool including, but not limited to, a cardiovascular catheter, a stent delivery and/or placement and/or retrieval tool, a balloon delivery and/or placement and/or retrieval tool, a valve delivery and/or repair and/or placement and/or retrieval tool, a graft delivery and/or placement and/or retrieval tool, a tool for the delivery and/or placement and/or retrieval of an implantable device or of parts of such a device, an implantable device or parts thereof, a tool for closing a gap, a tool for closing a septal defect, a guide wire, a marker wire, a suturing tool, a clipping tool (such as a valve-leaflet-clipping tool), a biopsy tool, an aspiration tool, a navigational tool, a localization tool, a probe comprising one or more location sensors, a tissue characterization probe, a probe for the analysis of fluid, a measurement probe, an electrophysiological probe, a stimulation probe, an ablation tool, a tool for penetrating or opening partial or total occlusions in blood vessels, a drug or substance delivery tool, a chemotherapy tool, a photodynamic therapy tool, a brachytherapy tool, a local irradiation tool, a laser device, a tool for delivering energy, a tool for delivering markers or biomarkers, a tool for delivering biological glue, an irrigation device, a suction device, a ventilation device, a device for delivering and/or placing and/or retrieving a lead of an electrophysiological device, a lead of an electrophysiological device, a pacing device, a coronary sinus device, an imaging device, a sensing probe, a probe comprising an optical fiber, a robotic tool, a tool that is controlled remotely, or any combination thereof.

The terms "image" and "imaging" refer to any type of medical imaging, typically presented as a sequence of images and including, but not limited to, imaging using ionizing radiation, imaging using non-ionizing radiation, video, fluoroscopy, angiography, ultrasound, CT, MR, PET, PET-CT, CT angiography, SPECT, Gamma camera imaging, Optical Coherence Tomography (OCT), Near-Infra-Red Spectroscopy (NIRS), Vibration Response Imaging (VRI), Optical Imaging, infrared imaging, electrical mapping imaging, other forms of Functional Imaging, or any combination or fusion thereof. Examples of ultrasound imaging include Endo-Bronchial Ultrasound (EBUS), Trans-Thoracic Echo (TTE), Trans-Esophageal Echo (TEE), Intra-Vascular Ultrasound (IVUS), Intra-Cardiac Ultrasound (ICE), or any combination thereof.

The term "contrast agent," when used in reference to its application in conjunction with imaging, refers to any substance that is used to highlight, and/or enhance in another manner, the anatomical structure, functioning, and/or composition of a bodily organ while the organ is being imaged.

The terms "lumen" and "cavity", refer to any lumen or cavity of the cardiovascular system, the gastro-intestinal tract, the respiratory tract, the urinary tract, the nasal cavities, and any other bodily lumen or cavity.

The term "stabilized," or "stable" when used in the context of displayed images, means a display of a series of images in a manner such that periodic, cyclical, and/or other motion of the body organ(s) being imaged, and/or of a medical tool being observed, is partially or fully reduced, with respect to the entire image frame, or at least a portion thereof.

The term "automatic," when used for describing background cleaning, means "without necessitating user intervention or interaction." (Such interaction or intervention may still however be optional in some cases.)

The term "real time" means without a noticeable delay.

The term "near real time" means with a short noticeable delay (such as approximately one or two motion cycles of an applicable organ, and, in the case of procedures relating to organs or vessels the motion of which are primarily as a result of the cardiac cycle, less than two seconds).

The term "on-line," when used in reference to image processing, or to measurements being made on images, means that the image processing is performed, and/or the measurements are made, intra-procedurally, in real time or near real time.

Figure 1B:
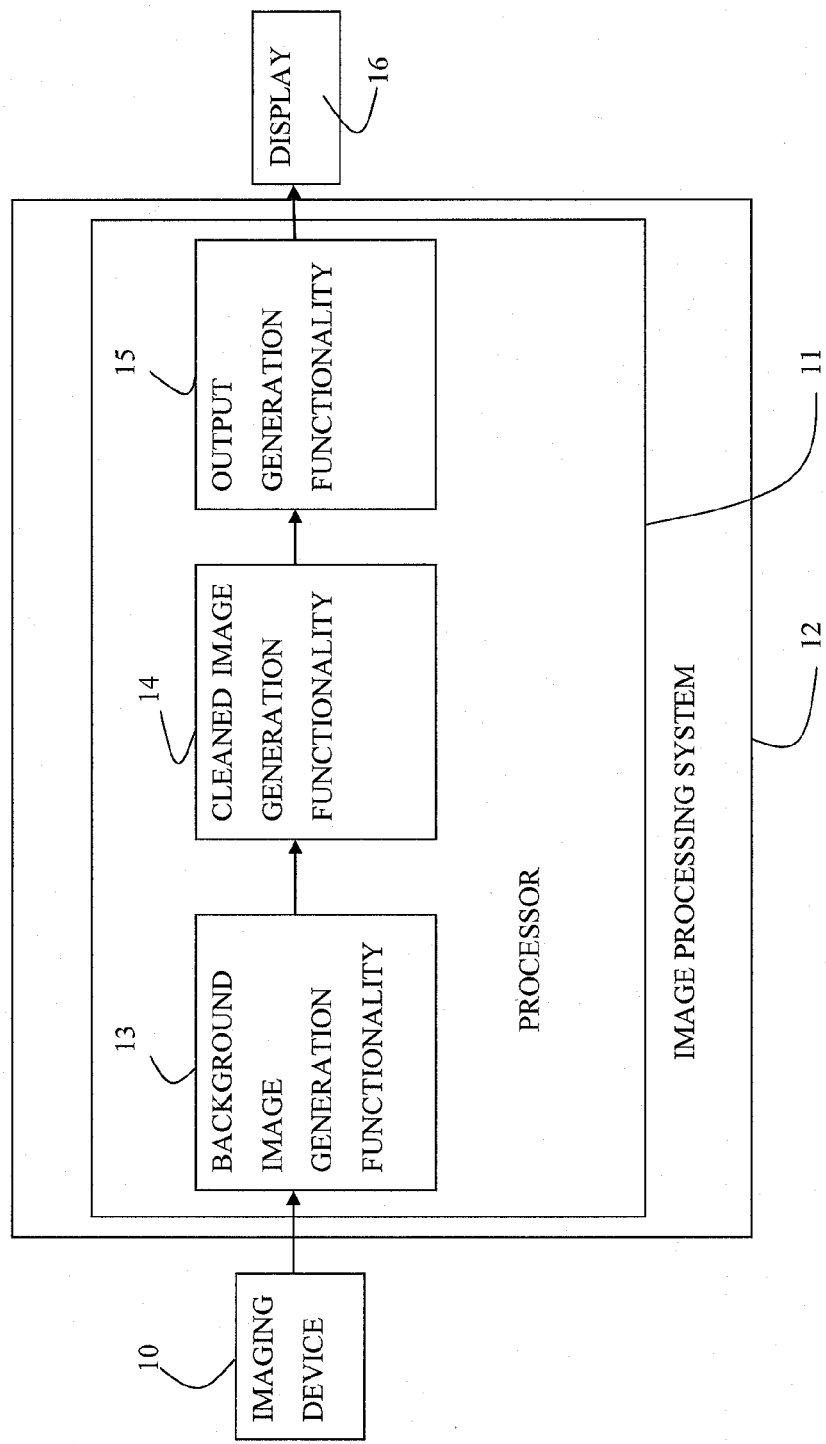
FIG. 1B is a block diagram showing components of an image-processing system, in accordance with some applications of the present invention.

References is now made to FIGS. 1A-1B, which are respectively (A) a flow chart, at least some of the steps of which are used to generate a cleaned luminal image from an input luminal image, in accordance with some applications of the present invention, and (B) a block diagram showing components of a processor of a an image-processing system, in accordance with some applications of the present invention. Applications of the present invention are typically used during medical procedures that are performed, in whole or in part, within body lumens or cavities. For some applications, apparatus and methods are provided for facilitating the visualization of a device positioned or deployed within such a lumen or cavity, at a time when the lumen or cavity is injected with contrast agent.

In accordance with some applications of the present invention, an input image acquired by an imaging device 10 (FIG. 1B) is input into a processor 11 of an image-processing system 12. Typically, within the input image, radiopaque portions of a tool inside a body lumen or a body cavity (and/or other are artifacts inside the lumen or the cavity) are hidden, in full or in part (e.g., are obscured), by contrast agent. The processor generates a cleaned image, in which visibility of the radiopaque portions of the tool (and/or the other artifacts) is improved relative to the input image. Typically, background-image-generation functionality 13 of the processor computes a background image. Subsequently, cleaned-image-generation functionality 14 of the processor divides the input image by the background image, such as to generate the cleaned image, in which visibility of the radiopaque portions of the tool (and/or the other artifacts) is improved relative to the input image. Typically, the cleaned image is generated from the input image automatically by the processor. Further typically, the generation of the cleaned image is performed by the processor on line, with respect to the inputting of the input image into the processor, and/or with respect to acquisition of the input image by an imaging device. Output generation functionality 15 of the processor typically drives a display 16 to display an output based on the cleaned image. For example, the display may display the cleaned image, or the display may display a stabilized image stream, the stabilization of the image stream being performed by performing image tracking based on locations of the radiopaque portions of the tool in the cleaned image.

Typically, in a first step, an input image $u_0$ (FIG. 1A) is inputted to processor 11, e.g., by the image being selected by the processor, or by a user. For some applications, the input image is a coronary angiogram, or a frame from an angiogram, that is acquired while a device that includes radiopaque sections thereof is within the coronary artery. For example, the device may be a balloon, a stent, a guide wire, an imaging probe, or any combination thereof. Typically, during injection of the contrast agent, the radiopaque sections of the device being inserted are hidden, in full or in part (e.g., obscured), by contrast agent.

Subsequent to the input image being inputted, a background image is generated by background-image-generation functionality 13, in accordance with the techniques described hereinbelow.

In the input image, pixels that are near to each other and that lie on the same object, are expected to have approximately the same value. For example, pixels lying on the ribs are expected to have approximately the same value as one another, and pixels lying inside a blood vessel are expected to have approximately the same value as one another. Thus, portions (i.e., pieces) of the input image are expected to have generally homogenous pixel values. However, the input image is not expected to be totally homogenous, since not all pixels lie on the same object. For example, pixels that lie on a rib are expected to have different values from pixels lying on a blood vessel. Thus, the values of the pixels in the input image can be assumed to be generally piecewise homogenous.

The assumption of piecewise homogeneity generally holds for the majority of the image pixels. However, the assumption fails to hold with respect to a portion of the pixels. An example of such pixels is that of the pixels that correspond to the radiopaque portions of an inserted device (e.g., radiopaque markers of a catheter). The values of such pixels are typically different from the values of their surrounding pixels, the surrounding pixels corresponding to the surrounding anatomy (e.g., a blood vessel in which the catheter is placed). Thus, these pixels are non-homogenous with respect to surrounding pixels.

For the purpose of the present invention, the non-homogeneous pixels are considered to be the foreground of the input image. An image that does not contain the non-homogeneous pixels (or in which the visibility of the non-homogeneous pixels is reduced), but which contains the piecewise homogenous pixels is considered to the background image. Thus, in accordance with the present invention, a background image is computed in which large contiguous piecewise homogenous image parts are enhanced relative to the input image, while the non-homogeneous pixels are made less visible relative to the input image. The background image is typically more homogeneous than the input image, and, in the background image, features of the subject's anatomy typically are enhanced relative to the input image, while the visibility of features of the tool is typically reduced relative to the input image.

The background image is typically computed by assigning a relative value to a first pixel in the background image with respect to a second pixel in the background image, based upon the relative values of the surroundings of the first pixel (e.g., a patch of pixels surrounding the first pixel) and the surroundings of the second pixel (e.g., a patch of pixels surrounding the first pixel) in the input image. Thus, pixels that have more similarly appearing surroundings in the input image are assigned more similar values to one another in the background image than pixels that have less similarly appearing surroundings in the input image. Typically, in computing the background image, the aforementioned method for assigning pixel values is traded-off against keeping the value of any given pixel in the background image similar to the value of the pixel in the input image.

For some applications, the background image is generated by computing a background image that is such as to reduce (e.g., that is such as to minimize) the cost of the following function:

$$\sum_x \left[ \frac{\lambda}{2}(b(x) - u_0(x))^2 + \sqrt{\sum_y (b(y) - b(x))^2 w(x, y) dy} \right] \quad \text{[Function 1]}$$

in which:
b(x) is the value of pixel x is the background image;
$u_0(x)$ is the value of pixel x in the input image;
b(y) is the value of pixel y is the background image;
w(x,y) is a weight measure that is the inverse of the weighted sum of the squared difference between $p_x$ (i.e., a patch taken around pixel x) and $p_y$ (i.e., a patch taken around pixel y).

The first term of Function 1 (i.e., the term in the brackets that appears before the "plus" sign) favors a background image whose pixel values are close to the pixel values of the input image. The second term of Function 1 (i.e., the term in the brackets that appears after the "plus" sign) favors a background image in which pixels the surroundings of which have similar values in the input image, have similar values in the background image. Thus, the resulting background image is typically similar to the input image, and at the same time is typically more homogenous than the input image, giving similar values to similar pixels. λ is a constant that represents the value of the trade-off between the first term and the second term of Function 1, i.e., the trade-off between (a) generating a background image in which the pixels have similar values to the values of the pixels in the input image and (b) generating an image in which the relative values of the pixels in the background image is based upon similarities between patches surrounding respective pixels in the input image. For some applications, the value of λ is set empirically, by testing different values on a wide range of benchmark input images.

For some applications, the background image is generated in accordance with minimization techniques described in "Nonlocal linear image regularization and supervised segmentation," by Guy Gilboa and Stanley Osher (SIAM Multiscale Modeling & Simulation, volume 6, issue 2, pp. 595630, 2007), and/or in "Nonlocal Operators with Applications to Image Processing," by Guy Gilboa and Stanley Osher (SIAM Multiscale Modeling & Simulation, volume 7, issue 3, pp. 1005-1028, 2008), both of which articles are incorporated herein by reference. Alternatively or additionally, other minimization techniques are used, such those described in "Nonlocal regularization of inverse problem," by Gabriel Peyre, Sebastien Bougleux, and Laurent Cohenin (Lecture Notes in Computer Science, 2008, Volume 5304/2008, pp. 57-68), "The split Bregman method for L1 regularized problems," by Tom Goldstein and Stanley Osher (SIAM Journal on Imaging Sciences, Volume 2, Issue 2, pp. 323-343), and/or in "Bregmanized nonlocal regularization for reconvolution and sparse reconstruction," by Xiaoqun Zhang, Martin Burgery, Xavier Bresson, and Stanley Osher (SIAM Journal on Imaging Sciences, Volume 3, Issue 3, July 2010), all of which articles are incorporated herein by reference.

For some applications, an algorithm as described in "Bregmanized nonlocal regularization for reconvolution and sparse reconstruction," by Zhang et al., which is incorporated herein by reference, is used to generate the background image. For example, algorithm 1 described on Page 17 of the aforementioned article may be used to generate the background image.

For some applications, the weight measure that is used to compute the background image (e.g., in accordance with Function 1, described hereinabove) is computed using the following technique. Given an input image, the processor of the system computes a weight measure between each pixel x in the image, and pixels in the vicinity of pixel x. The weight measure measures the similarity between small image patches centered on respective pixels x. For example, the similarity may be measured by an inverse of the weighted sum of squared differences between these patches. For some applications, the inverse of the weighted sum of squared differences is weighted by a Guassian, e.g., in accordance with techniques described in "A non-local algorithm for image denoising," by Buades, Coll and Morell (IEEE CVPR 2005, volume 2, pages 60-65), which is incorporated herein by reference.

Typically, subsequent to the generation of the background image of the lumen, a cleaned image is generated by cleaned-image-generation functionality 14, by dividing the input image by the background image. (It should be noted that, throughout the description of the present invention, "dividing the input image by the background image" should be interpreted as being synonymous with "subtracting the background image from the input image" with respect to the mathematical operations that are performed by processor 11.) Typically, in the resulting cleaned image, image elements which are not homogeneous inside the lumen (such as the radiopaque markers of the device inserted in the vessel) remain visible while the vessel itself appears, in whole or in part, "clean" of contrast agent, at least relative to the input image.

Although some of the techniques described herein have been described with reference to an angiogram of a device that in inserted the into the coronary artery, the scope of the present invention includes applying the techniques to images of other body lumen and/or body cavities, mutatis mutandis. For example, the techniques described herein may be applied to an angiogram of the aorta that has an aortic replacement valve placed therein. Alternatively or additionally, the techniques described herein may be applied to an angiogram of a heart chamber that has a replacement valve placed therein. Further alternatively or additionally, the techniques described herein may be applied to an angiogram of a heart ventricle that has a ventricular assist device placed therein.

Figure 2:
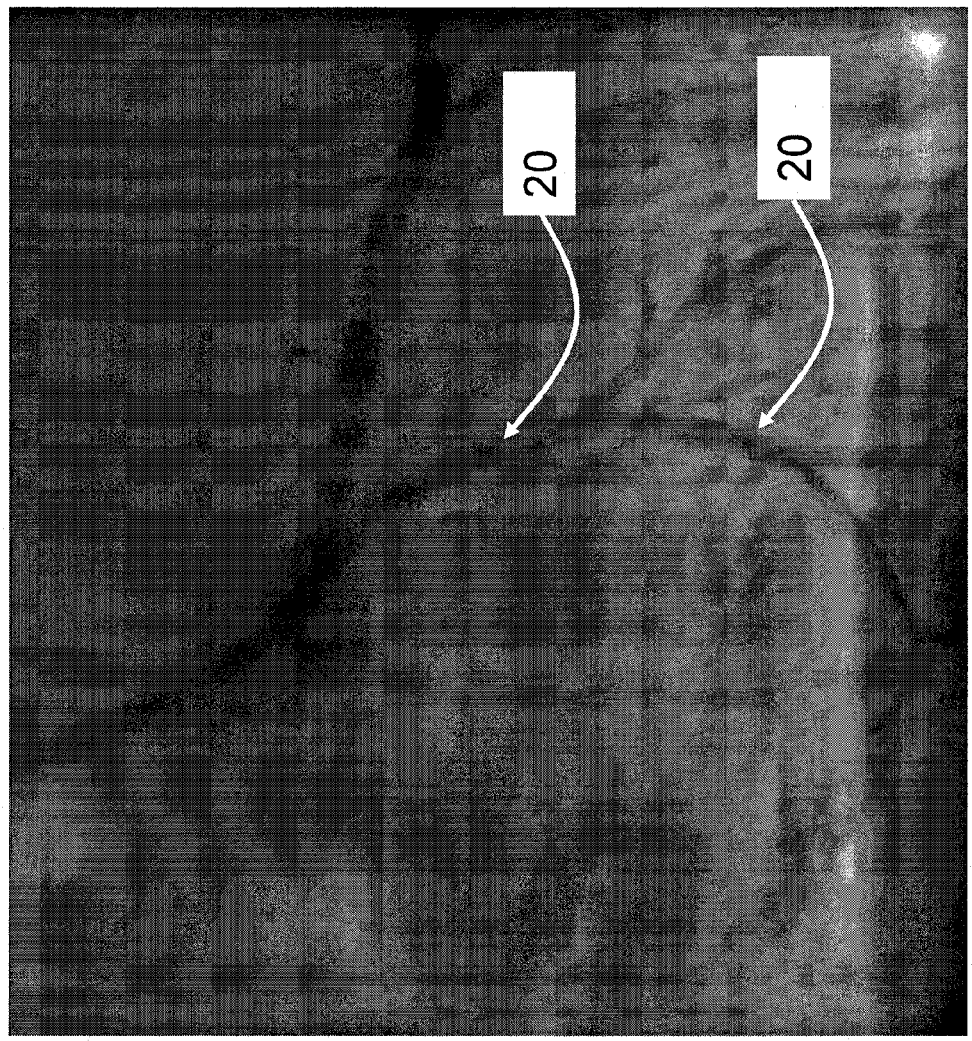
FIG. 2 shows an input luminal image, to which background cleaning may be subsequently applied, in accordance with some applications of the present invention.

Reference is now made to FIG. 2, which shows an example of input luminal image. Specifically, the image shown in FIG. 2 is a frame of an angiogram of a coronary artery in which a catheter carrying a stent is inserted. Two radiopaque markers 20 that are disposed on the catheter may be observed at the proximal and distal edges of a balloon on which the pre-deployed stent is mounted.

Figure 3:
FIG. 3 shows a background luminal image, generated in accordance with some applications of the present invention.

Reference is now made to FIG. 3, which is a background luminal image generated from the input image, typically automatically and typically on line, in accordance with techniques described hereinabove. In FIG. 3 the contrast-filled coronary artery is clearly visible, while the radiopaque elements of the catheter carrying the stent are not visible.

Figure 4:
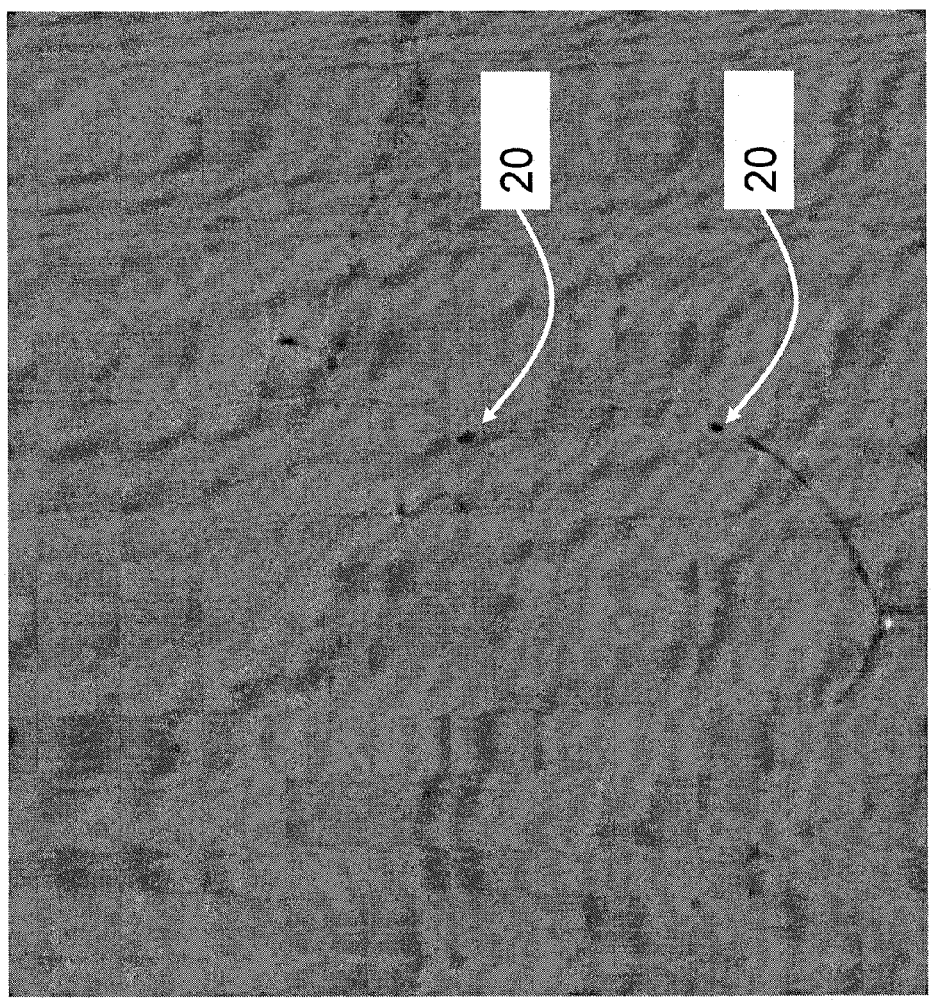
FIG. 4 shows a clean luminal image, generated in accordance with some applications of the present invention.

Reference is now made to FIG. 4, which is a cleaned image that was produced by dividing the input image by the background image, in accordance with the techniques described hereinabove. The cleaned image was generated automatically and on line with respect to the inputting of the input image to the system. It may be observed that in the cleaned image, the contrast-filled vessel is largely invisible, while radiopaque markers 20 of the catheter carrying the stent are seen more clearly than in the input image.

For some applications, a series of cleaned image frames are used to create a stabilized image stream of an angiographic sequence, in which, typically, radiopaque elements of a device (e.g., markers of a catheter carrying a stent) appear relatively stable. Typically, the stabilized image stream of the angiographic sequence is generated in accordance with techniques described in U.S. patent application Ser. No. 12/650,605 to Cohen (published as US 2010/0172556) and/or in U.S. patent application Ser. No. 12/075,244 to Tolkowsky (published as US 2008/0221442), both of which applications are incorporated herein by reference. The stabilized image stream is typically displayed on display 16. For some applications, a plurality of cleaned images are generated, the cleaned images corresponding to respective input images. The input images are stabilized such as to generate a stabilized image stream, based upon the locations of the radiopaque elements of the device in the corresponding cleaned images. Alternatively or additionally, a cleaned, stabilized image stream is generated by stabilizing the cleaned images with respect to each other, based upon the locations of the radiopaque elements of the device in the cleaned images.

For some applications, a stent is deployed within a lumen, and a catheter and/or a balloon carrying radiopaque markers remains within the luminal section in which the stent is deployed. A series of image frames are cleaned in accordance with the techniques described herein, and the cleaned image frames are used to create an enhanced image stream of an angiographic sequence, in which the stent appears more visible than in a native angiogram of the stent. Typically, the enhanced image stream is generated in accordance with techniques described herein, in combination with techniques described in U.S. patent application Ser. No. 12/650,605 to Cohen (published as US 2010/0172556), which is incorporated herein by reference. The enhanced image stream is typically displayed on display 16. For some applications, a plurality of cleaned images are generated, the cleaned images corresponding to respective input images. An enhanced image frame is generated by aligning the input images with each other based upon locations of the radiopaque portions of the device in the corresponding cleaned images, and generating an averaged image frame based upon the aligned input images. Alternatively or additionally, a cleaned, enhanced image frame is generated, by aligning the cleaned images with each other, based upon locations of the radiopaque portions of the device in the cleaned images, and generating an averaged image frame based upon the aligned cleaned images.

For some applications, a series of cleaned image frames are used to create an image stream that is both stabilized and enhanced. Typically, the stabilized, enhanced image stream of the angiographic sequence is generated in accordance with techniques described herein, in combination with techniques described in U.S. patent application Ser. No. 12/650,605 to Cohen (published as US 2010/0172556) and/or in U.S. patent application Ser. No. 12/075,244 to Tolkowsky (published as US 2008/0221442), both of which applications are incorporated herein by reference. The stabilized, enhanced image stream is typically displayed on display 16.

For some applications, a series of input image frames are divided by the respective corresponding background images such as to produce cleaned image frames. The cleaned image frames are used to create an image stream that is stabilized, enhanced and cleaned, by stabilizing and enhancing the cleaned image frames. In an embodiment, such an image stream is produced in accordance with techniques described herein, in combination with techniques described in U.S. patent application Ser. No. 12/650,605 to Cohen (published as US 2010/0172556) and/or in U.S. patent application Ser. No. 12/075,244 to Tolkowsky (published as US 2008/0221442), both of which applications are incorporated herein by reference. The stabilized, enhanced, cleaned image stream is typically displayed on display 16.

For some applications, the visibility of the radiopaque markers on an endoluminal device is increased in an image stream, by cleaning image frames belonging to the image stream, in accordance with the techniques described herein. The increased visibility of the markers is used to facilitate tracking the device comprising those markers, typically automatically and typically on line. Typically, the tracking is performed in accordance with techniques described in U.S. patent application Ser. No. 12/650,605 to Cohen (published as US 2010/0172556), which is incorporated herein by reference. For some applications, the endoluminal device comprising the radiopaque markers is an endoluminal data-acquisition device (e.g., an endoluminal imaging probe), and the increased visibility of the radiopaque markers in the resulting image stream is utilized for co-registering, typically automatically and typically on line, endoluminal data points (e.g., endoluminal images) with the extraluminal images (e.g., extraluminal x-ray images). The endoluminal imaging probe may be ultrasound, optical coherence, infrared, MRI, or any combination thereof. Typically, the co-registration is performed in accordance with techniques described in International Patent Application PCT/IL2011/000612 (published as WO 12/014,212), which is incorporated herein by reference.

For example, based upon locations of radiopaque portions of an endoluminal data-acquisition device in the cleaned image the output-generation functionality of the processor may determine that a given one of the endoluminal data points corresponds to a given location within the lumen, and an output may be generated in response thereto. Alternatively or additionally, based upon locations of the radiopaque portions of an endoluminal device in the cleaned image, the output-generation functionality may determine that the endoluminal device is at a given location within the lumen. In response to determining that the endoluminal device is at the given location within the lumen, the output-generation functionality may drive the display to display an endoluminal image of the lumen corresponding to the location.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with at least one input angiogram image of a device inserted inside a portion of a body of a subject, the device including radiopaque portions thereof, the angiogram image being acquired in the presence of contrast agent within the body portion, the apparatus comprising:

a display; and at least one processor configured:

to generate a background image in which a relative pixel value is assigned to a first pixel with respect to a second pixel, at least partially based upon relative pixel values of a patch of pixels that surround a first pixel of the input angiogram image that is disposed at the same location as the first pixel of the background image and a patch of pixels that surround a second pixel of the input angiogram image that is disposed at the same location as the second pixel of the background image;

to generate a cleaned image in which visibility of the radiopaque portions of the device is increased relative to the input angiogram image, by dividing the input angiogram image by the background image; and to drive the display to display an output based upon the cleaned image.

2. The apparatus according to claim 1, wherein the processor is configured to generate the background image by:

in the background image, assigning pixel values to the first pixel and the second pixel that are more similar to one another, than the similarity of pixel values that are assigned to a third pixel and a fourth pixel, based upon the patch of pixels that surround the first pixel of the input angiogram image and the patch of pixels that surround the second pixel of the input angiogram image having more similar pixel values to one another, than a similarity, to one another, of pixel values of a patch of pixels that surround a third pixel of the input angiogram image that is disposed at the same location as the third pixel of the background image and a patch of pixels that surround a fourth pixel of the input angiogram image that is disposed at the same location as the fourth pixel of the background image.

3. The apparatus according to claim 1, wherein the processor is further configured to generate the background image by assigning pixel values to the first and second pixels of the background image based upon pixel values of the first pixel and the second pixel of the input angiogram image.

4. The apparatus according to claim 1, wherein the processor is configured to drive the display to display the cleaned image.

5. The apparatus according to claim 1, wherein:
the input angiogram image of the device includes a plurality of input angiogram images of the device, and
the processor is configured to:
generate a plurality of cleaned images, the cleaned images corresponding to respective input angiogram images,
generate a stabilized image stream by image tracking the cleaned images with respect to each other, based upon locations of the radiopaque portions of the device in the cleaned images, and
drive the display to display the stabilized image stream.

6. The apparatus according to claim 1, wherein:
the input angiogram image of the device includes a plurality of input angiogram images of the device, and
the processor is configured to:
generate a plurality of cleaned images, the cleaned images corresponding to respective input angiogram images,
generate a stabilized image stream by image tracking the input images with respect to each other, based upon locations of the radiopaque portions of the device in the corresponding cleaned images, and
drive the display to display the stabilized image stream.

7. The apparatus according to claim 1, wherein:
the input angiogram image of the device includes a plurality of input angiogram images of the device, and
the processor is configured to:
generate a plurality of cleaned images, the cleaned images corresponding to respective input angiogram images,
generate an enhanced image frame by:
aligning the cleaned images with each other, based upon locations of the radiopaque portions of the device in the cleaned images, and
generating an averaged image frame based upon the aligned images, and
drive the display to display the enhanced image frame.

8. The apparatus according to claim 1, wherein:
the input angiogram image of the device includes a plurality of input angiogram images of the device, and
the processor is configured to:
generate a plurality of cleaned images, the cleaned images corresponding to respective input angiogram images,
generate an enhanced image frame by:
aligning the input images with each other, based upon locations of the radiopaque portions of the device in the corresponding cleaned images, and
generating an averaged image frame based upon the aligned images, and
drive the display to display the enhanced image frame.

9. The apparatus according to claim 1, wherein:
the portion of the subject's body includes a lumen of the subject's body,
the device includes an endoluminal data-acquisition device configured to acquire endoluminal data points while the device is at respective locations within the lumen, and
the processor is configured:
based upon locations of the radiopaque portions of the device in the cleaned image, to determine that a given one of the endoluminal data points corresponds to a given location within the lumen, and
to drive the display to display an output, in response to the determining.

10. The apparatus according to claim 1, wherein:
the portion of the subject's body includes a lumen of the subject's body,
the device includes an endoluminal device configured to be moved through the lumen, and
the processor is configured:
based upon locations of the radiopaque portions of the device in the cleaned image, to determine that the endoluminal device is at a given location within the lumen, and
in response to the determining that the endoluminal device is at the given location within the lumen, to drive the display to display an endoluminal image of the lumen corresponding to the location.

11. A method for use with at least one input angiogram image of a device inserted inside a portion of a body of a subject, the device including radiopaque portions thereof, the angiogram image being acquired in the presence of contrast agent within the body portion, the method comprising:
generating, with a processor, a background image in which a relative pixel value is assigned to a first pixel with respect to a second pixel, at least partially based upon relative pixel values of a patch of pixels that surround a first pixel of the input angiogram image that is disposed at the same location as the first pixel of the background image and a patch of pixels that surround a second pixel of the input angiogram image that is disposed at the same location as the second pixel of the background image;

generating, with the processor, a cleaned image in which visibility of the radiopaque portions of the device is increased relative to the input angiogram image, by dividing the input angiogram image by the background image; and generating an output on a display, based upon the cleaned image.

12. The method according to claim 11, wherein generating the background image comprises:
in the background image, assigning pixel values to the first pixel and the second pixel that are more similar to one another, than the similarity of pixel values that are assigned to a third pixel and a fourth pixel,
based upon the patch of pixels that surround the first pixel of the input angiogram image and the patch of pixels that surround the second pixel of the input angiogram image having more similar pixel values to one another, than a similarity, to one another, of pixel values of a patch of pixels that surround a third pixel of the input angiogram image that is disposed at the same location as the third pixel of the background image and a patch of pixels that surround a fourth pixel of the input angiogram image that is disposed at the same location as the fourth pixel of the background image.

13. The method according to claim 11, wherein generating the background image further comprises assigning pixel values to the first and second pixels of the background image based upon pixel values of the first pixel and the second pixel of the input angiogram image.

14. The method according to claim 11, wherein generating the output comprises displaying the cleaned image.

15. The method according to claim 11,
wherein the input angiogram image of the device includes a plurality of input angiogram images of the device,
wherein generating the cleaned image comprises generating a plurality of cleaned images, the cleaned images corresponding to respective input angiogram images,
the method further comprising generating a stabilized image stream by image tracking the cleaned images with respect to each other, based upon locations of the radiopaque portions of the device in the cleaned images, and
wherein generating the output comprises displaying the stabilized image stream.

16. The method according to claim 11,
wherein the input angiogram image of the device includes a plurality of input angiogram images of the device,
wherein generating the cleaned image comprises generating a plurality of cleaned images, the cleaned images corresponding to respective input angiogram images,
the method further comprising generating a stabilized image stream by image tracking the input images with respect to each other, based upon locations of the radiopaque portions of the device in the corresponding cleaned images, and
wherein generating the output comprises displaying the stabilized image stream.

17. The method according to claim 11,
wherein the input angiogram image of the device includes a plurality of input angiogram images of the device,
wherein generating the cleaned image comprises generating a plurality of cleaned images, the cleaned images corresponding to respective input angiogram images,
the method further comprising generating an enhanced image frame by:
aligning the cleaned images with each other, based upon locations of the radiopaque portions of the device in the cleaned images, and
generating an averaged image frame based upon the aligned cleaned images, and
wherein generating the output comprises displaying the enhanced image frame.

18. The method according to claim 11,
wherein the input angiogram image of the device includes a plurality of input angiogram images of the device,
wherein generating the cleaned image comprises generating a plurality of cleaned images, the cleaned images corresponding to respective input angiogram images,
the method further comprising generating an enhanced image frame by:
aligning the input images with each other, based upon locations of the radiopaque portions of the device in the corresponding cleaned images, and
generating an averaged image frame based upon the aligned input images, and
wherein generating the output comprises displaying the enhanced image frame.

19. The method according to claim 11,
wherein the portion of the subject's body includes a lumen of the subject's body,
wherein the device includes an endoluminal data-acquisition device configured to acquire endoluminal data points while the device is at respective locations within the lumen,
the method further comprising, based upon locations of the radiopaque portions of the device in the cleaned image, determining that a given one of the endoluminal data points corresponds to a given location within the lumen, and
wherein generating the output comprises generating the output in response to the determining.

20. The method according to claim 11,
wherein the portion of the subject's body includes a lumen of the subject's body,
wherein the device includes an endoluminal device configured to be moved through the lumen,
the method further comprising, based upon locations of the radiopaque portions of the device in the cleaned image, determining that the endoluminal device is at a given location within the lumen, and
wherein generating the output comprises, in response to the determining that the endoluminal device is at the given location within the lumen, generating an endoluminal image of the lumen corresponding to the location.

* * * * *